US009090610B2

(12) United States Patent
Follmann et al.

(10) Patent No.: US 9,090,610 B2
(45) Date of Patent: Jul. 28, 2015

(54) FLUOROALKYL-SUBSTITUTED PYRAZOLOPYRIDINES AND USE THEREOF

(75) Inventors: Markus Follmann, Köln (DE); Johannes-Peter Stasch, Solingen (DE); Gorden Redlich, Bochum (DE); Nils Griebenow, Dormagen (DE); Frank Wunder, Wuppertal (DE); Volkhart Min-Jian Li, Velbert (DE); Dieter Lang, Velbert (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/113,214

(22) PCT Filed: Apr. 20, 2012

(86) PCT No.: PCT/EP2012/057269
§ 371 (c)(1),
(2), (4) Date: Dec. 23, 2013

(87) PCT Pub. No.: WO2012/143510
PCT Pub. Date: Oct. 26, 2012

(65) Prior Publication Data
US 2014/0100229 A1 Apr. 10, 2014

(30) Foreign Application Priority Data

Apr. 21, 2011 (DE) .................. 10-2011-007-890
Jan. 11, 2012 (DE) .................. 10-2012-200-357

(51) Int. Cl.
*C07D 471/04* (2006.01)
*A61K 45/06* (2006.01)
*C07D 519/00* (2006.01)
*A61K 31/519* (2006.01)
*A61K 31/53* (2006.01)

(52) U.S. Cl.
CPC ............ *C07D 471/04* (2013.01); *A61K 31/519* (2013.01); *A61K 31/53* (2013.01); *A61K 45/06* (2013.01); *C07D 519/00* (2013.01)

(58) Field of Classification Search
CPC .............................. C07D 471/04; A61K 31/53
USPC ................................................. 544/184, 280
See application file for complete search history.

(56) References Cited

U.S. PATENT DOCUMENTS

| 5,976,523 A | 11/1999 | Awaya et al. |
| 6,180,656 B1 | 1/2001 | Fürstner et al. |
| 6,451,805 B1 | 9/2002 | Straub et al. |
| 6,743,798 B1 | 6/2004 | Straub et al. |
| 6,833,364 B1 | 12/2004 | Straub et al. |
| 6,903,089 B1 | 6/2005 | Stasch et al. |
| 7,173,037 B2 | 2/2007 | Alonso-Alija et al. |
| 7,410,973 B2 | 8/2008 | Feurer et al. |
| 7,414,136 B2 | 8/2008 | Matsumura et al. |
| 7,541,367 B2 | 6/2009 | Chiu et al. |
| 8,058,282 B2 | 11/2011 | Adams et al. |
| 8,242,272 B2 | 8/2012 | Jimenez et al. |
| 8,309,551 B2 | 11/2012 | Schirok et al. |
| 8,420,656 B2 | 4/2013 | Follmann et al. |
| 2004/0235863 A1 | 11/2004 | Feurer et al. |
| 2011/0218202 A1 | 9/2011 | Brockunier et al. |
| 2013/0072492 A1* | 3/2013 | Raghavan et al. ............ 514/248 |
| 2013/0172372 A1 | 7/2013 | Follmann et al. |
| 2013/0178475 A1 | 7/2013 | Moore et al. |
| 2013/0210824 A1 | 8/2013 | Follmann et al. |
| 2013/0338137 A1 | 12/2013 | Follmann et al. |
| 2014/0228366 A1* | 8/2014 | Follmann et al. ............ 514/243 |
| 2014/0350020 A1* | 11/2014 | Follmann et al. ............ 514/243 |
| 2014/0357637 A1* | 12/2014 | Follmann et al. ............ 514/243 |
| 2015/0065533 A1* | 3/2015 | Follmann et al. ............ 514/275 |
| 2015/0080414 A1* | 3/2015 | Follmann et al. ............ 514/256 |

FOREIGN PATENT DOCUMENTS

| CA | 2804470 A1 | 1/2012 |
| CA | 2834901 A1 | 11/2012 |
| CA | 2840886 A1 | 1/2013 |
| CN | 1613849 A | 5/2005 |
| EP | 0634413 A1 | 1/1995 |
| WO | 01083490 A1 | 11/2001 |
| WO | 02059083 A2 | 8/2002 |
| WO | WO 2010065275 A1 * | 6/2010 |
| WO | WO 2011149921 A1 * | 12/2011 |

OTHER PUBLICATIONS

International Preliminary Report on Patentability, PCT/EP2012/057269 (Oct. 22, 2013).*
F. Wunder et al., 339 Analytical Biochemistry, 104-112 (2005).*
T.L. Poulos et al., Current Opinion in Structural Biology, 736-743 (2006).*
A.J. Hobbs, 136 British Journal of Pharmacology (2002).*
R. Dumitrascu et al., 113 Circulation, 286-295 (2006).*
T.A. Michel, Treatment of Myocardial Ischemia In, Goodman & Gilman's: The Pharmacological Basis of Therapeutics, 823-844 (L.L. Brunton et al., eds., 11th ed., 2006).*
Becker et al.,"No-Independent Regulatory Site of Direct sGC Stimulators like YC-1 and Bay 41/2272," BMC Pharmacology, 2001, 1: 13.
Cheng et al.,"Potential Purine Antagonists VII. Synthesis of 6-Alkylpyrazolo-[3,4-d]pyrimidines," J. Org. Chem., 1958, 23:191-200.
Daley et al., The First Complete Identification of a Diastereomeric Catalyst-Substrate (Alkoxide) Species in an Enantioselective Ketone Hydrogenation. Mechanistic Investigations J. Am. Chem. Soc. 2002, 124(14):3680-3691.
Evgenov et al.,"No-independent stimulators and activators of soluble guanylate cyclase: discovery and therapeutic potential," Nat. Rev. Drug. Disc, Sep. 2006, 5:755-768.

(Continued)

*Primary Examiner* — Alexander R Pagano
(74) *Attorney, Agent, or Firm* — Buchanan Ingersoll & Rooney

(57) ABSTRACT

The present application relates to novel fluoroalkyl-substituted pyrazolopyridines, to processes for their preparation, to their use, alone or in combinations, for the treatment and/or prophylaxis of diseases and to their use for production of medicaments for the treatment and/or prophylaxis of diseases, especially for the treatment and/or prophylaxis of cardiovascular disorders.

5 Claims, No Drawings

(56) References Cited

OTHER PUBLICATIONS

Glass et al., "Stimulation of Human Platelet Guanylate Cyclase by Fatty Acids," J. Biol. Chem., Feb. 25, 1977, 252 (4):1279-1285.
Hassan et al.,"Aryl-Aryl Bond Formation One Century after the Discovery of the Ullmann Reaction," Chem. Rev. 2002, 102: 1359-1469.
Ko et al., "YC-1, a Novel Activator of Platelet Guanylate Cyclase," Blood, Dec.1994, 84(12): 4226-4233.
Maarten van den Buuse,"Circadian Rythyms of Blood Pressure, Heart Rate, and Locomotor Activity in Spontaneously Hypertensive Rats as Measured with Radio-Telemetry," Physiology & Behavior, 1994, 55(4):783-787.
Mittendorf et al., "Discovery of Riociguat (BAY 63-2521): A Potent, Oral Stimulator of Soluble Guanylate Cyclase for the Treatment of Pulmonary Hypertension," Chem. Med. Chem., 2009, 4: 853-865.
Malsch et al., "Effect of YC-1, an NO-independent, superoxide-sensitive stimulator of soluble guanylyl cyclase, on smooth muscle responsiveness to nitrovasodilators," Brit. J. Pharm., 1997, 120:681-689.
Pettibone et al., "A Structurally Novel Stimulator of Guanylate Cyclase with Long-Lasting Hypotensive Activity in the Dog," Euro. J. of Pharmacology, 1985, 116: 307-312.
Sharkovska et al.,"Nitric oxide-independent stimulation of soluble guanylate cyclase reduces organ damage in experimental low-renin and high-renin models," J. Hypertnesion, 2010, 28(8):1666-1675.
Stasch et al.,"Soluble Guanylate Cyclase as an Emerging Therapeutic Target in Cardiopulmonary Disease," Circulation, May 2011, 123: 2263-2273.
Straub et al., "No-Independent Stimulators of Soluble Guanylate Cyclase," Bioorg. Med. Chem. Lett., 2001, 11:781-784.
Wilson et al.,"Development of a Scaleable Synthesis of a Partial Nicotinic Acid Receptor Agonist," Organic Process Research & Development, 2009, 13: 543-547.
Winn et al., "2-(Alkylamino)nicotinic Acid and Analogs. Potent Angiotensin II Antagonists," J. Med. Chem 1993, 36: 2676-2688.
Witte et al.,"Experimental heart failure in rats: effects on cardiovascular circadian rhythms and on myocardial β-adrenergic signaling," Cardiovascular Research, 2000, 47: 350-358.
Wu et al., "YC-1 inhibited human platelet aggregation through No-independent activation of soluble guanylate cyclase," Br J. Pharmacol. Oct. 1995, 116(3):1973-1978.
Wunder et al., "A cell-based cGMP assay useful for ultra-high-throughput screening and identification of modulators of the nitric oxide/cGMP pathway," Anal. Biochem., 2005, 339:104-112.
Yu et al., "Vasorelaxant Effect of Isoliquiritigenin, A novel soluble guanylate cyclase activator, in rat aorta," Brit. J. of Pharmacology, 1995, 114: 1587-1594.
Badesch et al., "Prostanoid Therapy for Pulmonary Arterial Hypertension," Journal of the American College of Cardiology, Jun. 16, 2004, 43:56S-61S.
Ghofrani et al., "Soluble guanylate cyclase stimulation: an emerging option in pulmonary hypertension therapy," Eur. Respir. Rev., 2009, 18(111):35-41.
Freshney, R. Ian., "Culture of animal cells," A Manual of Basic Technique, Alan R. Liss, Inc., 1983, New York, p. 4.
Dermer, G. B., "Another Anniversary for the War on Cancer," Bio/Technology, 1994, 12:320.
Oudot et al., "Combination of Bay 60/4552 and Vardenafil Exerts Proerectile Facilitator Effects in Rats With Cavernous Nerve Injury: A Proof of Concept Study for the Treatment of Phosphodiesterase Type 5 Inhibitor Failure," European Urology, 2011, 60:1020-1026.
U.S. Appl. No. 13/704,980, 371(c) date Feb. 28, 2013, published as 20130172372.
U.S. Appl. No. 13/806,425.
U.S. Appl. No. 14/115,870, 371(c) date Feb. 5, 2014.
U.S. Appl. No. 14/131,017, 371(c) date Feb. 27, 2014.
U.S. Appl. No. 13/736,692, filed Jan. 8, 2013.
U.S. Appl. No. 13/599,975, filed Aug. 30, 2012.
U.S. Appl. No. 14/194,224, filed Feb. 28, 2014.
U.S. Appl. No. 14/371,054.
U.S. Appl. No. 14/371,046.
Toche et al., "Synthesis of Pyrazolopyridine 3-Carboxylates by Friedlander Condensation," J. Heterocyclic Chem., 2010, 47:287.

* cited by examiner

FLUOROALKYL-SUBSTITUTED PYRAZOLOPYRIDINES AND USE THEREOF

The present application relates to novel fluoroalkyl-substituted pyrazolopyridines, to processes for their preparation, to their use, alone or in combinations, for the treatment and/or prophylaxis of diseases and to their use for production of medicaments for the treatment and/or prophylaxis of diseases, especially for the treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family known to date can be divided into two groups either according to structural features or according to the type of ligands: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. This is of central importance for the activation mechanism. NO can bind to the iron atom of heme and thus markedly increase the activity of the enzyme. Heme-free preparations cannot, by contrast, be stimulated by NO. Carbon monoxide (CO) is also able to bind to the central iron atom of heme, but the stimulation by CO is much less than that by NO. By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disruption of the abovementioned processes. Under pathophysiological conditions, the NO/cGMP system can be suppressed, which can lead, for example, to hypertension, platelet activation, increased cell proliferation, endothelial dysfunction, atherosclerosis, angina pectoris, heart failure, myocardial infarction, thromboses, stroke and sexual dysfunction.

Owing to the expected high efficiency and low level of side effects, a possible NO-independent treatment for such disorders by targeting the influence of the cGMP signal pathway in organisms is a promising approach.

Therapeutic stimulation of soluble guanylate cyclase has to date been accomplished using exclusively compounds such as organic nitrates, the effect of which is based on NO. The latter is formed by bioconversion and activates soluble guanylate cyclase by attack at the central iron atom of heme. In addition to the side effects, the development of tolerance is one of the crucial disadvantages of this mode of treatment.

In recent years, some substances have been described which stimulate soluble guanylate cyclase directly, i.e. without prior release of NO, such as, for example, 3-(5'-hydroxymethyl-2'-furyl)-1-benzylindazole [YC-1; Wu et al., Blood 84 (1994), 4226; Mülsch et al., Brit. J. Pharmacol. 120 (1997), 681], fatty acids [Goldberg et al., J. Biol. Chem. 252 (1977), 1279], diphenyliodonium hexafluorophosphate [Pettibone et al., Eur. J. Pharmacol. 116 (1985), 307], isoliquiritigenin [Yu et al., Brit. J. Pharmacol. 114 (1995), 1587] and various substituted pyrazole derivatives (WO 98/16223).

As stimulators of soluble guanylate cyclase, WO 00/06569 discloses fused pyrazole derivatives, and WO 03/095451 carbamate-substituted 3-pyrimidinylpyrazolopyridines. WO 2010/065275 and WO 2011/149921 disclose substituted pyrrolo- and dihydropyridopyrimidines as sGC activators.

It is an object of the present invention to provide novel substances which act as stimulators of soluble guanylate cyclase and which have an identical or improved therapeutic profile compared to compounds known from the prior art, for example with respect to their in vivo properties such as their pharmacokinetic and pharmacodynamic behavior and/or their metabolic profile and/or their dose-activity relationship.

The present invention provides compounds of the general formula (I)

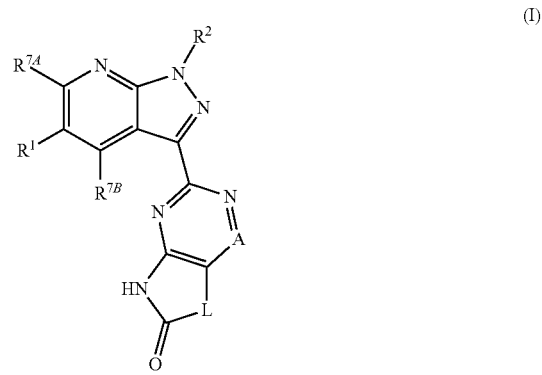

in which
A is nitrogen or $CR^3$
  where
  $R^3$ is hydrogen, deuterium, halogen, difluoromethyl, trifluoromethyl, $(C_1-C_4)$-alkyl, $(C_2-C_4)$-alkenyl, $(C_2-C_4)$-alkynyl, cyclopropyl, cyclobutyl, hydroxy, phenyl or 5- or 6-membered heteroaryl,
    in which $(C_1-C_4)$-alkyl, $(C_2-C_4)$-alkenyl, $(C_2-C_4)$-alkynyl, phenyl and 5- or 6-membered heteroaryl may be substituted by 1 to 3 substituents independently of one another selected from the group consisting of fluorine, difluoromethyl, trifluoromethyl, $(C_1-C_4)$-alkyl, difluoromethoxy, trifluoromethoxy, $(C_1-C_4)$-alkoxy, $(C_1-C_4)$-alkoxycarbonyl, cyclopropyl and cyclobutyl,
L is a #-$CR^{4A}R^{4B}$—$(CR^{5A}R^{5B})_p$-## group
  where
  # is the point of attachment to the carbonyl group,
  ## is the point of attachment to the pyrimidine ring or triazine ring,
  p is a number 0, 1 or 2,
  $R^{4A}$ is hydrogen, fluorine, $(C_1-C_4)$-alkyl, hydroxy or amino,
    in which $(C_1-C_4)$-alkyl may be substituted by 1 to 3 substituents independently of one another selected from the group consisting of fluorine, trifluoromethyl, hydroxy, hydroxycarbonyl, $(C_1-C_4)$-alkoxycarbonyl and amino,
  $R^{4B}$ is hydrogen, fluorine, difluoromethyl, trifluoromethyl, $(C_1-C_6)$-alkyl, $(C_1-C_4)$-alkoxycarbonylamino, cyano, $(C_3-C_7)$-cycloalkyl, difluoromethoxy, trifluoromethoxy, phenyl or a group of the formula -M-$R^8$,
    in which $(C_1-C_6)$-alkyl may be substituted by 1 to 3 substituents independently of one another selected from the group consisting of fluorine, cyano, trifluoromethyl, $(C_3-C_7)$-cycloalkyl, hydroxy, difluoromethoxy, trifluoromethoxy, $(C_1-C_4)$-alkoxy, hydroxycarbonyl, $(C_1-C_4)$-alkoxycarbonyl and amino, and in which M is a bond or $(C_1-C_4)$-alkanediyl, $R^8$ is $-(C=O)_r-OR^9$, $-(C=O)_r-NR^9R^{10}$, $-C(=S)-NR^9R^{10}$, $-NR^9-(C=O)-R^{12}$, $-NR^9-(C=O)-NR^{10}R^{11}$, $-NR^9-SO_2-NR^{10}R^{11}$, $-NR^9-SO_2-R^{12}$, $-S(O)_s-R^{12}$, $-SO_2-NR^9R^{10}$, 4- to 7-membered heterocyclyl, phenyl or 5- or 6-membered heteroaryl, in which r is the number 0 or 1, s is the number 0, 1 or 2, $R^9$, $R^{10}$ and $R^{11}$ independently of one another are each hydrogen, $(C_1-C_6)$-alkyl, $(C_3-C_8)$-cycloalkyl, 4- to 7-membered heterocyclyl, phenyl or 5- or 6-membered heteroaryl, or $R^9$ and $R^{10}$ together with the atom(s) to which they are attached form a 4- to 7-membered heterocycle, in which the 4- to 7-membered heterocycle for its part may be substituted by 1 or 2 substituents independently of one another selected from the group consisting of cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di-$(C_1-C_6)$-alkylamino, or $R^{10}$ and $R^{11}$ together with the atom(s) to which they are attached form a 4- to 7-membered heterocycle, in which the 4- to 7-membered heterocycle for its part may be substituted by 1 or 2 substituents independently of one another selected from the group consisting of cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di-$(C_1-C_6)$-alkylamino, $R^{12}$ is $(C_1-C_6)$-alkyl or $(C_3-C_7)$-cycloalkyl, or $R^9$ and $R^{12}$ together with the atom(s) to which they are attached form a 4- to 7-membered heterocycle, in which the 4- to 7-membered heterocycle for its part may be substituted by 1 or 2 substituents independently of one another selected from the group consisting of cyano, trifluoromethyl, $(C_1-C_6)$-alkyl, hydroxy, oxo, $(C_1-C_6)$-alkoxy, trifluoromethoxy, $(C_1-C_6)$-alkoxycarbonyl, amino, mono-$(C_1-C_6)$-alkylamino and di-$(C_1-C_6)$-alkylamino, and in which 4- to 7-membered heterocyclyl, phenyl and 5- or 6-membered heteroaryl for their part may be substituted by 1 to 3 substituents independently of one another selected from the group consisting of halogen, cyano, difluoromethyl, trifluoromethyl, $(C_1-C_6)$-alkyl, $(C_3-C_7)$-cycloalkyl, hydroxy, oxo, thioxo and $(C_1-C_4)$-alkoxy, and in which the aforementioned $(C_1-C_4)$-alkyl, $(C_1-C_6)$-alkyl, $(C_3-C_8)$-cycloalkyl and 4- to 7-membered heterocyclyl groups, unless stated otherwise, may each independently of one another additionally be substituted by 1 to 3 substituents independently of one another selected from the group consisting of fluorine, difluoromethyl, trifluoromethyl, $(C_1-C_6)$-alkyl, $(C_3-C_7)$-cycloalkyl, hydroxy, difluoromethoxy, trifluoromethoxy, $(C_1-C_4)$-alkoxy, hydroxycarbonyl, $(C_1-C_4)$-alkoxycarbonyl, amino, phenyl, 4- to 7-membered heterocyclyl and 5- or 6-membered heteroaryl, or $R^{4A}$ and $R^{4B}$ together with the carbon atom to which they are attached form a $(C_2-C_4)$-alkenyl group, an oxo group, a 3- to 6-membered carbocycle or a 4- to 7-membered heterocycle, in which the 3- to 6-membered carbocycle and the 4- to 7-membered heterocycle may be substituted by 1 or 2 substituents independently of one another selected from the group consisting of fluorine and $(C_1-C_4)$-alkyl, $R^{5A}$ is hydrogen, fluorine, $(C_1-C_4)$-alkyl or hydroxy, $R^{5B}$ is hydrogen, fluorine, $(C_1-C_4)$-alkyl or trifluoromethyl, $R^1$ is hydrogen, halogen, cyano, difluoromethyl, trifluoromethyl, $(C_1-C_4)$-alkyl or $(C_3-C_7)$-cycloalkyl, $R^2$ is a group of the formula $*-(CR^{6A}R^{6B})_q CHF_2$, $*-(CR^{6A}R^{6B})_q CF_3$ or $*-(CR^{6A}R^{6B})_q-(C_3-C_7)$-cycloalkyl, where

* is the point of attachment to the pyrazolopyridine, q is a number 1, 2 or 3, $R^{6A}$ is hydrogen or fluorine, $R^{6B}$ is hydrogen or fluorine, and where $(C_3-C_7)$-cycloalkyl may be substituted by 1 to 3 substituents independently of one another selected from the group consisting of fluorine and $(C_1-C_4)$-alkyl, $R^{7A}$ is hydrogen, cyano, difluoromethyl, trifluoromethyl, $(C_1-C_4)$-alkyl or $(C_3-C_7)$-cycloalkyl, $R^{7B}$ is hydrogen, cyano, difluoromethyl, trifluoromethyl, $(C_1-C_4)$-alkyl or $(C_3-C_7)$-cycloalkyl, and the N-oxides, salts, solvates, salts of the N-oxides and solvates of the N-oxides or salts thereof.

Compounds according to the invention are the compounds of the formula (I) and their salts, solvates and solvates of the salts, the compounds, comprised by formula (I), of the formulae mentioned below and their salts, solvates and solvates of the salts and the compounds comprised by formula (I), mentioned below as working examples, and their salts, solvates and solvates of the salts, if the compounds, comprised by formula (I), mentioned below are not already salts, solvates and solvates of the salts.

Compounds according to the invention are likewise N-oxides of the compounds of the formula (I) and the salts, solvates and solvates of the salts thereof.

Preferred salts in the context of the present invention are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g.

calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates refer to those forms of the compounds according to the invention which, in the solid or liquid state, form a complex by coordination with solvent molecules. Hydrates are a specific form of solvates in which the coordination is with water. Solvates preferred in the context of the present invention are hydrates.

The compounds according to the invention may, depending on their structure, exist in different stereoisomeric forms, i.e. in the form of configurational isomers or else optionally as conformational isomers (enantiomers and/or diastereomers, including those in the case of atropisomers). The present invention therefore encompasses the enantiomers and diastereomers, and the respective mixtures thereof. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than that which occurs usually or predominantly in nature. Examples of isotopes which can be incorporated into a compound according to the invention are those of hydrogen, carbon, nitrogen, oxygen, phosphorus, sulfur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$S, $^{82}$Br, $^{123}$I, $^{124}$I, $^{129}$I and $^{131}$I. Particular isotopic variants of a compound according to the invention, such as, more particularly, those in which one or more radioactive isotopes have been incorporated, may be of benefit, for example, for the study of the mechanism of action or of the active compound distribution in the body; due to the comparative ease of preparability and detectability, compounds labeled particularly with $^3$H or $^{14}$C isotopes are suitable for this purpose. Furthermore, the incorporation of isotopes, for example of deuterium, can lead to particular therapeutic advantages as a consequence of greater metabolic stability of the compound, for example an extension of the half-life in the body or a reduction in the active dose required; such modifications of the compounds according to the invention may therefore, in some cases, also constitute a preferred embodiment of the present invention. Isotopic variants of the compounds according to the invention can be prepared by the processes known to those skilled in the art, for example by the methods described below and the procedures described in the working examples, by using corresponding isotopic modifications of the respective reagents and/or starting compounds.

Moreover, the present invention also encompasses prodrugs of the compounds according to the invention. Here, the term "prodrugs" refers to compounds which for their part can be biologically active or inactive, but are converted (for example metabolically or hydrolytically) into compounds according to the invention during their dwell time in the body.

In the formula of the group that L or $R^2$ may represent, the end point of the line marked by the symbol #, ## or * does not represent a carbon atom or a $CH_2$ group but is part of the bond to the respective atom to which L or $R^2$ is bonded.

In the context of the present invention, the substituents, unless specified otherwise, are each defined as follows:

Alkyl in the context of the invention is a straight-chain or branched alkyl radical having the number of carbon atoms specified in each case. The following may be mentioned by way of example and by way of preference: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl and 2-ethylbutyl.

Cycloalkyl or carbocycle in the context of the invention is a monocyclic saturated alkyl radical having the number of carbon atoms specified in each case. The following may be mentioned by way of example and by way of preference: cyclopropyl, cyclobutyl, cyclopentyl, cyclohexyl and cycloheptyl.

Alkanediyl in the context of the invention is a straight-chain or branched divalent alkyl radical having 1 to 4 carbon atoms. The following may be mentioned by way of example and by way of preference: methylene, ethane-1,2-diyl, ethane-1,1-diyl, propane-1,3-diyl, propane-1,1-diyl, propane-1,2-diyl, propane-2,2-diyl, butane-1,4-diyl, butane-1,2-diyl, butane-1,3-diyl and butane-2,3-diyl.

Alkenyl in the context of the invention is a straight-chain or branched alkenyl radical having 2 to 4 carbon atoms and a double bond. The following may be mentioned by way of example and by way of preference: vinyl, allyl, isopropenyl and n-but-2-en-1-yl.

Alkynyl in the context of the invention is a straight-chain or branched alkynyl radical having 2 to 4 carbon atoms and one triple bond. The following may be mentioned by way of example and by way of preference: ethynyl, n-prop-1-yn-1-yl, n-prop-2-yn-1-yl, n-but-2-yn-1-yl and n-but-3-yn-1-yl.

Alkoxy in the context of the invention is a straight-chain or branched alkoxy radical having 1 to 6 or 1 to 4 carbon atoms. The following may be mentioned by way of example: methoxy, ethoxy, n-propoxy, isopropoxy, 1-methylpropoxy, n-butoxy, isobutoxy, tert-butoxy, n-pentoxy, isopentoxy, 1-ethylpropoxy, 1-methylbutoxy, 2-methylbutoxy, 3-methylbutoxy and n-hexoxy. Preference is given to a straight-chain or branched alkoxy radical having 1 to 4 carbon atoms. The following may be mentioned by way of example and by way of preference: methoxy, ethoxy, n-propoxy, isopropoxy, 1-methylpropoxy, n-butoxy, isobutoxy, tert-butoxy.

Alkoxycarbonyl in the context of the invention is a straight-chain or branched alkoxy radical having 1 to 4 carbon atoms and a carbonyl group attached to the oxygen. The following may be mentioned by way of example and by way of preference: methoxycarbonyl, ethoxycarbonyl, n-propoxycarbonyl, isopropoxycarbonyl and tert-butoxycarbonyl.

Alkoxycarbonylamino in the context of the invention is an amino group having a straight-chain or branched alkoxycarbonyl substituent which has 1 to 4 carbon atoms in the alkyl chain and is attached via the carbonyl group to the nitrogen atom. The following may be mentioned by way of example and by way of preference: methoxycarbonylamino, ethoxycarbonylamino, propoxycarbonylamino, n-butoxycarbonylamino, isobutoxycarbonylamino and tert-butoxycarbonylamino.

Monoalkylamino in the context of the invention is an amino group having a straight-chain or branched alkyl substituent having 1 to 6 carbon atoms. The following may be mentioned by way of example and by way of preference: methylamino, ethylamino, n-propylamino, isopropylamino and tert-butylamino.

Dialkylamino in the context of the invention is an amino group having two identical or different, straight-chain or branched alkyl substituents each having 1 to 6 carbon atoms. The following may be mentioned by way of example and by way of preference: N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino.

Heterocyclyl or heterocycle in the context of the invention is a saturated heterocycle which has a total of 4 to 7 ring atoms and contains one or two ring heteroatoms from the group consisting of N, O, S, SO and/or $SO_2$. The following may be mentioned by way of example: azetidinyl, oxetanyl, pyrrolidinyl, pyrazolidinyl, imidazolinyl, tetrahydrofuranyl, piperidinyl, piperazinyl, tetrahydropyranyl, morpholinyl, thiomorpholinyl and dioxidothiomorpholinyl. Preference is given to azetidinyl, oxetanyl, pyrrolidinyl, tetrahydrofuranyl, piperidinyl, tetrahydropyranyl and morpholinyl.

5- or 6-membered heteroaryl in the context of the invention is a monocyclic aromatic heterocycle (heteroaromatic) which has a total of 5 or 6 ring atoms, contains up to three identical or different ring heteroatoms from the group consisting of N, O and/or S and is attached via a ring carbon atom or optionally via a ring nitrogen atom. The following may be mentioned by way of example and by way of preference: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl and triazinyl. Preference is given to: pyrazolyl, oxazolyl, thiazolyl, triazolyl, oxadiazolyl, thiadiazolyl, pyridyl and pyrimidinyl.

Halogen in the context of the invention is fluorine, chlorine, bromine and iodine. Preference is given to bromine and iodine.

An oxo group in the context of the invention is an oxygen atom bonded via a double bond to a carbon atom.

A thioxo group in the context of the invention is a sulfur atom bonded via a double bond to a carbon atom.

When radicals in the compounds according to the invention are substituted, the radicals, unless specified otherwise, may be mono- or polysubstituted. In the context of the present invention, all radicals which occur more than once are defined independently of one another. Substitution by one, two or three identical or different substituents is preferred.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development or progression of such states and/or the symptoms of such states.

The treatment or prevention of a disease, a condition, a disorder, an injury or a health problem may be partial or complete.

The compounds of the formula (I-1) form a sub-group of the compounds of the formula (I) according to the invention in which $R^{7A}$ and $R^{7B}$ are hydrogen.

In the context of the present invention, preference is given to compounds of the formula (I) in which A is nitrogen or $CR^3$,
  where
    $R^3$ is hydrogen, deuterium, fluorine, iodine, difluoromethyl, trifluoromethyl, $(C_1-C_4)$-alkyl, vinyl, allyl, ethynyl, cyclopropyl, cyclobutyl, hydroxy, pyrazolyl or pyridyl,
    where $(C_1-C_4)$-alkyl, vinyl, allyl, ethynyl and pyridyl may be substituted by 1 or 2 substituents independently of one another selected from the group consisting of methyl, cyclopropyl and cyclobutyl, L is a #-$CR^{4A}R^{4B}$—$(CR^{5A}R^{5B})_p$-## group
  where
    # is the point of attachment to the carbonyl group,
    ## is the point of attachment to the pyrimidine ring or triazine ring,
    p is a number 0 or 1,
    $R^{4A}$ is hydrogen, fluorine, methyl, ethyl, hydroxy or amino,
    $R^{4B}$ is hydrogen, fluorine, difluoromethyl, trifluoromethyl, $(C_1-C_4)$-alkyl, methoxycarbonylamino, cyano, cyclopropyl, cyclobutyl, cyclopentyl, phenyl or a group of the formula -M-$R^8$,
      in which $(C_1-C_4)$-alkyl may be substituted by 1 to 3 substituents independently of one another selected from the group consisting of fluorine, cyano, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino,
      and in which
      M is a bond or methylene,
      $R^8$ is —$(C=O)_r$—$NR^9R^{10}$, —$C(=S)$—$NR^9R^{10}$, oxadiazolonyl, oxadiazolethionyl, phenyl, oxazolyl, thiazolyl, pyrazolyl, triazolyl, oxadiazolyl, thiadiazolyl, pyridyl, pyrimidinyl or pyrazinyl,
        in which
        r is the number 0 or 1,
        $R^9$ and $R^{10}$ are each independently of one another hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl,
          in which methyl, ethyl and isopropyl for their part may be substituted by 1 or 2 substituents independently of one another selected from the group consisting of fluorine, difluoromethyl, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino,
          and
          in which oxadiazolonyl, oxadiazolethionyl, phenyl, oxazolyl, thiazolyl, pyrazolyl, triazolyl, oxadiazolyl, thiadiazolyl, pyridyl, pyrimidinyl and pyrazinyl for their part may be substituted by 1 or 2 substituents independently of one another selected from the group consisting of fluorine, chlorine, cyano, difluoromethyl, trifluoromethyl, methyl, ethyl, isopropyl, 2,2,2-trifluoroethyl, 1,1,2,2- pentafluoroethyl, cyclopropyl, cyclobutyl, cyclopropylmethyl, cyclobutylmethyl, hydroxy, methoxy and ethoxy, or $R^{4A}$ and $R^{4B}$ together with the carbon atom to which they are attached form a cyclopropyl, cyclobutyl, cyclopentyl, azetidinyl, tetrahydrofuranyl, pyrrolidinyl or tetrahydropyranyl ring, in which the cyclopropyl, cyclobutyl, cyclopentyl, azetidinyl, tetrahydrofuranyl, pyrrolidinyl and tetrahydropyranyl ring may be substituted by 1 or 2 substituents independently of one another selected from the group consisting of fluorine and methyl, $R^{5A}$ is hydrogen, fluorine, methyl, ethyl or hydroxy, $R^{5B}$ is hydrogen, fluorine, methyl, ethyl or trifluoromethyl, $R^1$ is hydrogen or fluorine, $R^2$ is a group of the formula *—$(CR^{6A}R^{6B})_q$CHF$_2$, *—$(CR^{6A}R^{6B})_q$CF$_3$, cyclobutylmethyl or cyclopentylmethyl, where

* is the point of attachment to the pyrazolopyridine, q is a number 2 or 3, $R^{6A}$ is hydrogen or fluorine, $R^{6B}$ is hydrogen or fluorine, and where cyclobutylmethyl and cyclopentylmethyl may be substituted by 1 or 2 fluorine substituents, $R^{7A}$ is hydrogen or methyl, $R^{7B}$ is hydrogen, and the salts, solvates and solvates of the salts thereof.

In the context of the present invention, preference is also given to compounds of the formula (I) in which A is nitrogen or $CR^3$, where $R^3$ represents hydrogen, L is a #-$CR^{4A}R^{4B}$—$(CR^{5A}R^{5B})_p$-## group where # is the point of attachment to the carbonyl group, ## is the point of attachment to the pyrimidine ring or triazine ring, p is a number 0 or 1, $R^{4A}$ is hydrogen, fluorine, methyl, ethyl, hydroxy or amino, $R^{4B}$ is hydrogen, fluorine, difluoromethyl, trifluoromethyl, methyl, ethyl, methoxycarbonylamino, cyclopropyl, cyclobutyl, cyclopentyl or a group of the formula -M-$R^8$, in which methyl and ethyl may be substituted by 1 to 3 substituents independently of one another selected from the group consisting of fluorine, cyano, trifluoromethyl, cyclopropyl, cyclobutyl, hydroxy, difluoromethoxy, trifluoromethoxy, methoxy, ethoxy, hydroxycarbonyl, methoxycarbonyl, ethoxycarbonyl and amino, and in which M is a bond, $R^8$ is —(C=O)$_r$—NR$^9$R$^{10}$, phenyl, thiazolyl, triazolyl, oxadiazolyl, thiadiazolyl or pyrimidinyl, in which r is the number 1, $R^9$ and $R^{10}$ independently of one another are each hydrogen or cyclopropyl, and in which phenyl, thiazolyl, triazolyl, oxadiazolyl, thiadiazolyl and pyrimidinyl for their part may be substituted by 1 or 2 substituents independently of one another selected from the group consisting of fluorine, difluoromethyl, trifluoromethyl, methyl, ethyl, isopropyl, 2,2,2-trifluoroethyl, 1,1,2,2-pentafluoroethyl, cyclopropyl, cyclobutyl, cyclopropylmethyl and cyclobutylmethyl, or $R^{4A}$ and $R^{4B}$ together with the carbon atom to which they are attached form a cyclopropyl, cyclobutyl, cyclopentyl, azetidinyl, tetrahydrofuranyl, pyrrolidinyl or tetrahydropyranyl ring, in which the cyclopropyl, cyclobutyl, cyclopentyl, azetidinyl, tetrahydrofuranyl, pyrrolidinyl and tetrahydropyranyl ring may be substituted by 1 or 2 substituents independently of one another selected from the group consisting of fluorine and methyl, $R^{5A}$ is hydrogen, fluorine, methyl or hydroxy, $R^{5B}$ is hydrogen, fluorine, methyl or trifluoromethyl, $R^1$ is hydrogen or fluorine, $R^2$ is 3,3,3-trifluoroprop-1-yl, 4,4,4-trifluorobut-1-yl, 3,3,4,4-tetrafluorobut-1-yl, 3,3,4,4,4-pentafluorobut-1-yl, cyclobutylmethyl or cyclopentylmethyl, where cyclobutylmethyl and cyclopentylmethyl may be substituted by 1 or 2 fluorine substituents, $R^{7A}$ is hydrogen or methyl, $R^{7B}$ is hydrogen, and the salts, solvates and solvates of the salts thereof.

In the context of the present invention, particular preference is given to compounds of the formula (I) in which A is nitrogen or $CR^3$, where $R^3$ represents hydrogen, L is a #-$CR^{4A}R^{4B}$—$(CR^{5A}R^{5B})_p$-## group where # is the point of attachment to the carbonyl group, ## is the point of attachment to the pyrimidine ring or triazine ring,

P is a number O, $R^{4A}$ is hydrogen, fluorine, methyl or hydroxy, $R^{4B}$ is hydrogen, fluorine, trifluoromethyl, 2,2,2-trifluoroethyl, methyl or a group of the formula -M-$R^8$, in which M is a bond, $R^8$ is —(C=O)$_r$—NR$^9$R$^{10}$, in which r is the number 1, $R^9$ and $R^{10}$ independently of one another are each hydrogen or cyclopropyl, $R^1$ is hydrogen or fluorine, $R^2$ is 4,4,4-trifluorobut-1-yl, 3,3,4,4-tetrafluorobut-1-yl, 3,3,4,4,4-pentafluorobut-1-yl, cyclobutylmethyl or cyclopentylmethyl, where cyclobutylmethyl and cyclopentylmethyl may be substituted by 1 or 2 fluorine substituents, $R^{7A}$ is hydrogen or methyl, $R^{7B}$ is hydrogen, and the salts, solvates and solvates of the salts thereof.

In the context of the present invention, preference is given to compounds of the formula (I-1)

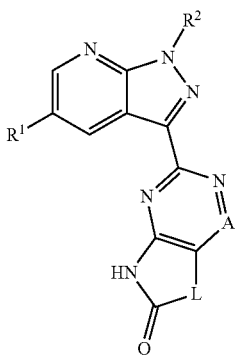

(I-1)

in which
A is nitrogen or $CR^3$,
where
$R^3$ is hydrogen, deuterium, fluorine, difluoromethyl, trifluoromethyl, $(C_1-C_4)$-alkyl, cyclopropyl or cyclobutyl,
L is a #-$CR^{4A}R^{4B}$—$(CR^{5A}R^{5B})_p$-## group
where
# is the point of attachment to the carbonyl group,
## is the point of attachment to the pyrimidine or triazine ring,
p is a number 0, 1 or 2,
$R^{4A}$ is hydrogen, fluorine, $(C_1-C_4)$-alkyl, hydroxy or amino,
$R^{4B}$ is hydrogen, fluorine, $(C_1-C_4)$-alkyl, trifluoromethyl, $(C_1-C_4)$-alkoxycarbonylamino or phenyl,
in which $(C_1-C_4)$-alkyl may be substituted by 1 to 3 substituents independently of one another selected from the group consisting of fluorine, trifluoromethyl, hydroxy, hydroxycarbonyl and $(C_1-C_4)$-alkoxycarbonyl,
or
$R^{4A}$ and $R^{4B}$ together with the carbon atom to which they are attached form an oxo group, a 3- to 6-membered carbocycle or a 4- to 6-membered heterocycle,
in which the 3- to 6-membered carbocycle and the 4- to 6-membered heterocycle may be substituted by 1 or 2 substituents independently of one another selected from the group consisting of fluorine and $(C_1-C_4)$-alkyl,
or
$R^{4A}$ and $R^{4B}$ together with the carbon atom to which they are attached form a $(C_2-C_4)$-alkenyl group,
$R^{5A}$ is hydrogen, fluorine, $(C_1-C_4)$-alkyl or hydroxy,
$R^{5B}$ is hydrogen, fluorine, $(C_1-C_4)$-alkyl or trifluoromethyl,
$R^1$ is hydrogen or fluorine,
$R^2$ is a group of the formula *—$(CR^{6A}R^{6B})_qCF_3$,
where
* is the point of attachment to the pyrazolopyridine,
q is a number 1, 2 or 3,
$R^{6A}$ is hydrogen or fluorine,
$R^{6B}$ is hydrogen or fluorine,
and the salts, solvates and solvates of the salts thereof.

Preference is given in the context of the present invention to compounds of the formula (I-1) in which
A is nitrogen or $CR^3$,
where
$R^3$ is hydrogen, fluorine, difluoromethyl, trifluoromethyl, methyl, ethyl or cyclopropyl,
L is a #-$CR^{4A}R^{4B}$—$(CR^{5A}R^{5B})_p$-## group where
# is the point of attachment to the carbonyl group,
## is the point of attachment to the pyrimidine or triazine ring,
p is a number 0 or 1,
$R^{4A}$ is hydrogen, fluorine, methyl, ethyl or hydroxy,
$R^{4B}$ is hydrogen, fluorine, methyl, ethyl, trifluoromethyl, methoxycarbonylamino or phenyl,
in which methyl and ethyl may be substituted by 1 to 3 substituents independently of one another selected from the group consisting of fluorine, trifluoromethyl and hydroxy,
or
$R^{4A}$ and $R^{4B}$ together with the carbon atom to which they are attached form a cyclopropyl, cyclobutyl, cyclopentyl, azetidinyl, pyrrolidinyl, tetrahydrofuranyl, piperidinyl or tetrahydropyranyl ring,
in which the cyclopropyl, cyclobutyl, cyclopentyl, azetidinyl, pyrrolidinyl, tetrahydrofuranyl, piperidinyl and tetrahydropyranyl ring may be substituted by 1 or 2 substituents independently of one another selected from the group consisting of fluorine and methyl,
$R^{5A}$ is hydrogen, fluorine, methyl, ethyl or hydroxy,
$R^{5B}$ is hydrogen, fluorine, methyl, ethyl or trifluoromethyl,
$R^1$ is hydrogen or fluorine,
$R^2$ is 2,2,2-trifluoroethyl, 3,3,3-trifluoroprop-1-yl, 4,4,4-trifluorobut-1-yl or 3,3,4,4,4-pentafluorobut-1-yl,
and the salts, solvates and solvates of the salts thereof.

In the context of the present invention, particular preference is given to compounds of the formula (I-1) in which
A is $CR^3$,
where
$R^3$ represents hydrogen,
L is a #-$CR^{4A}R^{4B}$—$(CR^{5A}R^{5B})_p$-## group
where
# is the point of attachment to the carbonyl group,
## is the point of attachment to the pyrimidine ring,
p is a number 0,
$R^{4A}$ is hydrogen, fluorine, methyl or hydroxy,
$R^{4B}$ is hydrogen, fluorine, methyl or trifluoromethyl,
or
$R^{4A}$ and $R^{4B}$ together with the carbon atom to which they are attached form a cyclopropyl or cyclobutyl ring,
in which the cyclopropyl and the cyclobutyl ring may be substituted by 1 or 2 substituents independently of one another selected from the group consisting of fluorine and methyl,
$R^1$ is hydrogen or fluorine,
$R^2$ is 3,3,4,4,4-pentafluorobut-1-yl,
and the salts, solvates and solvates of the salts thereof.

In the context of the present invention, particular preference is also given to compounds of the formula (I) in which
A is nitrogen,
L is a #-$CR^{4A}R^{4B}$—$(CR^{5A}R^{5B})_p$-## group
where
# is the point of attachment to the carbonyl group,
## is the point of attachment to the triazine ring,
p is a number 0,
$R^{4A}$ is hydrogen, fluorine, methyl or hydroxy,
$R^{4B}$ is hydrogen, fluorine, methyl or trifluoromethyl,
or
$R^{4A}$ and $R^{4B}$ together with the carbon atom to which they are attached form a cyclopropyl or cyclobutyl ring,
in which the cyclopropyl and the cyclobutyl ring may be substituted by 1 or 2 substituents independently of one another selected from the group consisting of fluorine and methyl, R$^1$ is hydrogen or fluorine, R$^2$ is 3,3,4,4,4-pentafluorobut-1-yl, and the salts, solvates and solvates of the salts thereof.

Preference is also given in the context of the present invention to compounds of the formula (I) and (I-1) in which R$^1$ is H, and the salts, solvates and solvates of the salts thereof.

Preference is also given in the context of the present invention to compounds of the formula (I) and (I-1) in which R$^1$ is fluorine, and the salts, solvates and solvates of the salts thereof.

Preference is also given in the context of the present invention to compounds of the formula (I) and (I-1) in which A is N or CH, and the salts, solvates and solvates of the salts thereof.

Preference is also given in the context of the present invention to compounds of the formula (I) and (I-1) in which A is CH, and the salts, solvates and solvates of the salts thereof.

Preference is also given in the context of the present invention to compounds of the formula (I) and (I-1) in which A is N, and the salts, solvates and solvates of the salts thereof.

Preference is also given in the context of the present invention to compounds of the formula (I) and (I-1) in which L is a #-CR$^{4A}$R$^{4B}$—(CR$^{5A}$R$^{5B}$)$_p$-## group where # is the point of attachment to the carbonyl group, ## is the point of attachment to the pyrimidine or triazine ring, p is a number 0, R$^{4A}$ and R$^{4B}$ together with the carbon atom to which they are attached form a cyclopropyl, cyclobutyl, cyclopentyl, azetidinyl, pyrrolidinyl, tetrahydrofuranyl, piperidinyl or tetrahydropyranyl ring, and the salts, solvates and solvates of the salts thereof.

Preference is also given in the context of the present invention to compounds of the formula (I) and (I-1) in which L is a #-CR$^{4A}$R$^{4B}$—(CR$^{5A}$R$^{5B}$)$_p$-## group where # is the point of attachment to the carbonyl group, ## is the point of attachment to the pyrimidine or triazine ring, p is a number 0, R$^{4A}$ and R$^{4B}$ together with the carbon atom to which they are attached form an azetidinyl, pyrrolidinyl, tetrahydrofuranyl, piperidinyl or tetrahydropyranyl ring, and the salts, solvates and solvates of the salts thereof.

Preference is also given in the context of the present invention to compounds of the formula (I) and (I-1) in which L is a #-CR$^{4A}$R$^{4B}$—(CR$^{5A}$R$^{5B}$)$_p$-## group where # is the point of attachment to the carbonyl group, ## is the point of attachment to the pyrimidine or triazine ring, p is a number 0, R$^{4A}$ is hydrogen, fluorine, methyl or hydroxy, R$^{4B}$ is hydrogen, fluorine, methyl or trifluoromethyl, and the salts, solvates and solvates of the salts thereof.

Preference is also given in the context of the present invention to compounds of the formula (I) and (I-1) in which L is a #-CR$^{4A}$R$^{4B}$—(CR$^{5A}$R$^{5B}$)$_p$-## group where # is the point of attachment to the carbonyl group, ## is the point of attachment to the pyrimidine or triazine ring, p is a number 0, R$^{4A}$ is hydrogen, fluorine, methyl, hydroxy or amino, R$^{4B}$ is hydrogen, fluorine, methyl, trifluoromethyl, 2,2,2-trifluoroethyl or 1,1,2,2,2-pentafluoroethyl, and the salts, solvates and solvates of the salts thereof.

Preference is also given in the context of the present invention to compounds of the formula (I) and (I-1) in which L is a #-CR$^{4A}$R$^{4B}$—(CR$^{5A}$R$^{5B}$)$_p$-## group where # is the point of attachment to the carbonyl group, ## is the point of attachment to the pyrimidine or triazine ring, p is a number 0, R$^{4A}$ is hydroxy or amino, R$^{4B}$ is trifluoromethyl, 2,2,2-trifluoroethyl or 1,1,2,2,2-pentafluoroethyl, and the salts, solvates and solvates of the salts thereof.

Preference is also given in the context of the present invention to compounds of the formula (I) and (I-1) in which L is a #-CR$^{4A}$R$^{4B}$—(CR$^{5A}$R$^{5B}$)$_p$-## group where # is the point of attachment to the carbonyl group, ## is the point of attachment to the pyrimidine or triazine ring, p is a number 0, R$^{4A}$ is methyl, R$^{4B}$ is methyl, and the salts, solvates and solvates of the salts thereof.

Preference is also given in the context of the present invention to compounds of the formula (I) and (I-1) in which L is a #-CR$^{4A}$R$^{4B}$—(CR$^{5A}$R$^{5B}$)$_p$-## group where # is the point of attachment to the carbonyl group, ## is the point of attachment to the pyrimidine or triazine ring, p is a number 0, R$^{4A}$ and R$^{4B}$ together with the carbon atom to which they are attached form a cyclopropyl or cyclobutyl ring, in which the cyclopropyl and the cyclobutyl ring may be substituted by 1 or 2 substituents independently of one another selected from the group consisting of fluorine and methyl, and the salts, solvates and solvates of the salts thereof.

Preference is also given in the context of the present invention to compounds of the formula (I) and (I-1) in which R$^2$ is 3,3,4,4,4-pentafluorobut-1-yl, and the salts, solvates and solvates of the salts thereof.

Preference is also given in the context of the present invention to compounds of the formula (I) in which A is nitrogen, L is a #-CR$^{4A}$R$^{4B}$—(CR$^{5A}$R$^{5B}$)$_p$-## group where # is the point of attachment to the carbonyl group, ## is the point of attachment to the triazine ring, p is a number 0,

R$^{4A}$ is hydrogen, fluorine, methyl or hydroxy,

R$^{4B}$ is hydrogen, fluorine, trifluoromethyl, 2,2,2-trifluoroethyl or methyl, and the salts, solvates and solvates of the salts thereof.

Preference is also given in the context of the present invention to compounds of the formula (I) in which A is CR$^3$, where R$^3$ represents hydrogen, L is a #-CR$^{4A}$R$^{4B}$—(CR$^{5A}$R$^{5B}$)$_p$-## group where # is the point of attachment to the carbonyl group, ## is the point of attachment to the pyrimidine ring, p is a number 0,

R$^{4A}$ is hydrogen, fluorine, methyl or hydroxy,

R$^{4B}$ is hydrogen, fluorine, trifluoromethyl, 2,2,2-trifluoroethyl or methyl, and the salts, solvates and solvates of the salts thereof.

Preference is also given in the context of the present invention to compounds of the formula (I) in which A is $CR^3$,
where
$R^3$ represents hydrogen,
L is a #-$CR^{4A}R^{4B}$—$(CR^{5A}R^{5B})_p$-## group
where
# is the point of attachment to the carbonyl group,
## is the point of attachment to the pyrimidine ring,
p is a number 0,
$R^{4A}$ is hydrogen, fluorine, methyl, ethyl, hydroxy or amino,
$R^{4B}$ is a group of the formula -M-$R^8$,
in which
M is a bond,
$R^8$ is —(C=O)$_r$—$NR^9R^{10}$, —C(=S)—$NR^9R^{10}$, oxadiazolonyl, oxadiazolethionyl, phenyl, oxazolyl, thiazolyl, pyrazolyl, triazolyl, oxadiazolyl, thiadiazolyl, pyridyl, pyrimidinyl or pyrazinyl,
in which
r is the number 0,
$R^9$ and $R^{10}$ are each independently of one another hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl,
in which methyl, ethyl and isopropyl for their part may be substituted by 1 or 2 substituents independently of one another selected from the group consisting of fluorine, difluoromethyl, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino,
and
in which oxadiazolonyl, oxadiazolethionyl, phenyl, oxazolyl, thiazolyl, pyrazolyl, triazolyl, oxadiazolyl, thiadiazolyl, pyridyl, pyrimidinyl and pyrazinyl for their part may be substituted by 1 or 2 substituents independently of one another selected from the group consisting of fluorine, chlorine, cyano, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl, cyclobutylmethyl, hydroxy, methoxy and ethoxy, and the salts, solvates and solvates of the salts thereof.

Preference is also given in the context of the present invention to compounds of the formula (I) in which A is N,
L is a #-$CR^{4A}R^{4B}$—$(CR^{5A}R^{5B})_p$-## group
where
# is the point of attachment to the carbonyl group,
## is the point of attachment to the triazine ring,
p is a number 0,
$R^{4A}$ is hydrogen, fluorine, methyl, ethyl, hydroxy or amino,
$R^{4B}$ is a group of the formula -M-$R^8$,
in which
M is a bond,
$R^8$ is —(C=O)$_r$—$NR^9R^{10}$, —C(=S)—$NR^9R^{10}$, oxadiazolonyl, oxadiazolethionyl, phenyl, oxazolyl, thiazolyl, pyrazolyl, triazolyl, oxadiazolyl, thiadiazolyl, pyridyl, pyrimidinyl or pyrazinyl,
in which
r is the number 0,
$R^9$ and $R^{10}$ are each independently of one another hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl,
in which methyl, ethyl and isopropyl for their part may be substituted by 1 or 2 substituents independently of one another selected from the group consisting of fluorine, difluoromethyl, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino,
and
in which oxadiazolonyl, oxadiazolethionyl, phenyl, oxazolyl, thiazolyl, pyrazolyl, triazolyl, oxadiazolyl, thiadiazolyl, pyridyl, pyrimidinyl and pyrazinyl for their part may be substituted by 1 or 2 substituents independently of one another selected from the group consisting of fluorine, chlorine, cyano, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl, cyclobutylmethyl, hydroxy, methoxy and ethoxy, and the salts, solvates and solvates of the salts thereof.

The individual radical definitions specified in the particular combinations or preferred combinations of radicals are, independently of the particular combinations of the radicals specified, also replaced as desired by radical definitions of other combinations.

Particular preference is given to combinations of two or more of the preferred ranges mentioned above.

The invention further provides a process for preparing the compounds of the formula (I) according to the invention, characterized in that a compound of the formula (II)

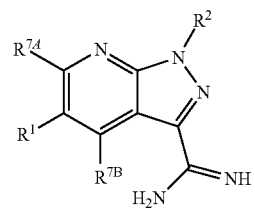

(II)

in which $R^1$, $R^2$, $R^{7A}$ and $R^{7B}$ each have the meanings given above,

[A] is reacted in an inert solvent in the presence of a suitable base with a compound of the formula (III)

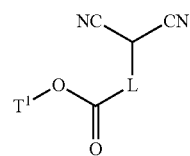

(III)

in which L has the meaning given above and
$T^1$ is ($C_1$-$C_4$)-alkyl,
to give a compound of the formula (IV)

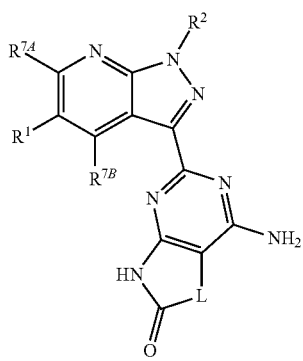
(IV)

in which L, $R^1$, $R^2$, $R^{7A}$ and $R^{7B}$ each have the meanings given above,
this is then converted with isopentyl nitrite and a halogen equivalent into a compound of the formula (V)

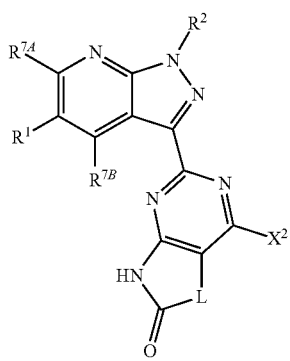
(V)

in which L, $R^1$, $R^2$, $R^{7A}$ and $R^{7B}$ each have the meanings given above and
$X^2$ is bromine or iodine,
and this is then reacted in an inert solvent, in the presence of a suitable transition metal catalyst, to give a compound of the formula (I-A)

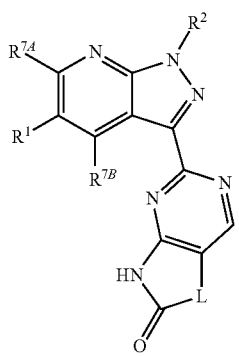
(I-A)

in which L, $R^1$, $R^2$, $R^{7A}$ and $R^{7B}$ each have the meanings given above,
or
[B] is reacted in an inert solvent in the presence of a suitable base with hydrazine hydrate to give a compound of the formula (VI)

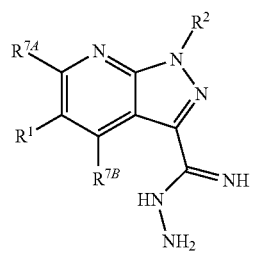
(VI)

in which $R^1$, $R^2$, $R^{7A}$ and $R^{7B}$ each have the meanings given above,
this is then reacted in an inert solvent with a compound of the formula (VII)

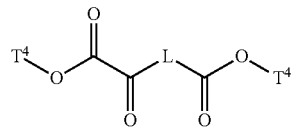
(VII)

in which L has the meaning given above and
$T^4$ is $(C_1-C_4)$-alkyl
to give a compound of the formula (VIII)

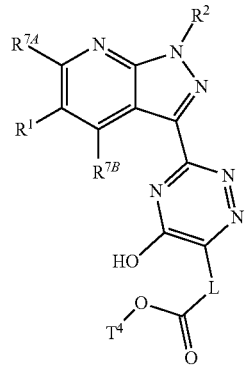
(VIII)

in which L, $R^1$, $R^2$, $R^{7A}$, $R^{7B}$ and $T^4$ each have the meanings given above,
this is then converted with phosphoryl chloride into a compound of the formula (IX)

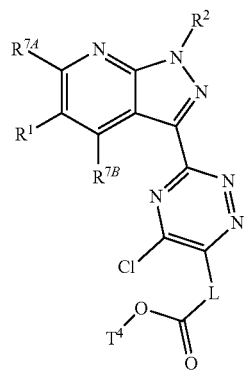
(IX)

in which L, $R^1$, $R^2$, $R^{7A}$, $R^{7B}$ and $T^4$ each have the meanings given above,
and this is reacted directly with ammonia to give a compound of the formula (X)

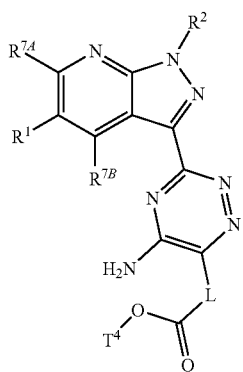

(X)

in which L, $R^1$, $R^2$, $R^{7A}$, $R^{7B}$ and $T^4$ each have the meanings given above,
and finally cyclized in an inert solvent, optionally in the presence of a suitable base, to give a compound of the formula (I-B)

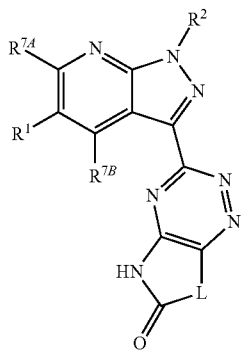

(I-B)

in which L, $R^1$, $R^2$, $R^{7A}$ and $R^{7B}$ each have the meanings given above,
and the resulting compounds of the formulae (I-A) and (I-B) are, where appropriate, converted with the appropriate (i) solvents and/or (ii) acids or bases into their solvates, salts and/or solvates of the salts.

The compounds of the formulae (I-A) and (I-B) together form the group of the compounds of the formula (I) according to the invention.

Inert solvents for the process step (II)+(III) are, for example, alcohols such as methanol, ethanol, n-propanol, isopropanol, n-butanol or tert-butanol, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), pyridine, acetonitrile, sulfolane or else water. It is also possible to use mixtures of the solvents mentioned. Preference is given to tert-butanol or methanol.

Suitable bases for the process step (II)+(III) are alkali metal hydroxides such as, for example, lithium hydroxide, sodium hydroxide or potassium hydroxide, alkali metal carbonates such as lithium carbonate, sodium carbonate, potassium carbonate or cesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to potassium tert-butoxide or sodium methoxide.

The reaction (II)+(III) is generally carried out in a temperature range of from +20° C. to +150° C., preferably at from +75° C. to +100° C., optionally in a microwave. The reaction can be carried out at atmospheric, elevated or reduced pressure (for example from 0.5 to 5 bar). The reaction is generally carried out at atmospheric pressure.

Process step (IV)→(V) is carried out with or without solvent. Suitable solvents are all organic solvents which are inert under the reaction conditions. A preferred solvent is dimethoxyethane.

The reaction (IV)→(V) is generally carried out in a temperature range of from +20° C. to +100° C., preferably within the range from +50° C. to +100° C., optionally in a microwave. The reaction can be performed at atmospheric, elevated or reduced pressure (for example in the range from 0.5 to 5 bar). The reaction is generally carried out at atmospheric pressure.

Suitable halogen sources in the reaction (IV)→(V) are, for example, diiodomethane, a mixture of cesium iodide, iodine and copper(I) iodide or copper(II) bromide.

Process step (IV)→(V), in the case of diiodomethane as the halogen source, is carried out with a molar ratio of 10 to 30 mol of isopentyl nitrite and 10 to 30 mol of the iodine equivalent based on 1 mol of the compound of the formula (IV).

Inert solvents for the process step (V)→(I-A) are alcohols such as methanol, ethanol, n-propanol, isopropanol, n-butanol, tert-butanol or 1,2-ethanediol, ethers such as diethyl ether, dioxane, tetrahydrofuran, glycol dimethyl ether or diethylene glycol dimethyl ether, or other solvents such as dimethylformamide (DMF), N,N'-dimethylpropyleneurea (DMPU), N-methylpyrrolidone (NMP), pyridine or else water. It is also possible to use mixtures of the solvents mentioned. Preference is given to DMF.

The reduction (V)→(I-A) is carried out with hydrogen in conjunction with transition metal catalysts, for example palladium (10% on activated carbon), Raney nickel or palladium hydroxide.

The reaction (V)→(I-A) is generally carried out in a temperature range of from +20° C. to +50° C. The reaction can be performed at atmospheric or elevated pressure (for example in the range from 0.5 to 5 bar). The reaction is generally carried out at atmospheric pressure.

The reaction (VIII)→(IX) can be effected in a solvent which is inert under the reaction conditions, or without solvent. A preferred solvent is sulfolane.

The reaction (VIII)→(IX) is generally carried out in a temperature range of from +70° C. to +150° C., preferably from +80° C. to +130° C., optionally in a microwave. The reaction can be performed at atmospheric or elevated pressure (for example in the range from 0.5 to 5 bar). The reaction is generally carried out at atmospheric pressure.

Especially preferably, the reaction (VIII)→(IX) is effected without solvent in a temperature range from 0° C. to +50° C. at atmospheric pressure.

Process step (IX)→(X) is carried out in a solvent which is inert under the reaction conditions. Suitable solvents are, for example, ethers such as diethyl ether, dioxane, tetrahydrofuran, glycol dimethyl ether or diethylene glycol dimethyl ether, or other solvents such as dimethylformamide (DMF), dimethyl sulfoxide (DMSO), N,N'-dimethylpropyleneurea (DMPU), N-methylpyrrolidone (NMP), pyridine, acetonitrile or else water. It is also possible to use mixtures of the solvents mentioned. Preference is given to acetonitrile.

The reaction (IX)→(X) is generally carried out in a temperature range of from +20° C. to +100° C., preferably from +40° C. to +70° C., optionally in a microwave. The reaction can be performed at atmospheric or elevated pressure (for example in the range from 0.5 to 5 bar). The reaction is generally carried out at atmospheric pressure.

The cyclization (X)→(I-B) is carried out in a solvent which is inert under the reaction conditions, for example alcohols such as methanol, ethanol, n-propanol, isopropanol, n-butanol or tert-butanol, ethers such as diethyl ether, dioxane, dimethoxyethane, tetrahydrofuran (THF), glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), pyridine, acetonitrile or sulfolane. It is also possible to use mixtures of the solvents mentioned. Preference is given to THF.

Suitable bases for the process step (X)→(I-B) are alkali metal hydroxides such as, for example, lithium hydroxide, sodium hydroxide or potassium hydroxide, alkali metal carbonates such as lithium carbonate, sodium carbonate, potassium carbonate or cesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to potassium tert-butoxide.

The reaction (X)→(I-B) is generally carried out in a temperature range of from 0° C. to +50° C., preferably from +10° C. to +30° C., optionally in a microwave. The reaction can be performed at atmospheric or elevated pressure (for example in the range from 0.5 to 5 bar). The reaction is generally carried out at atmospheric pressure.

The cyclization to give (I-B) is preferably carried out directly in the course of the reaction (IX)→(X) without addition of further reagents.

In an alternative procedure for process [B], the conversion (VI)+(VII)→(VIII)→(IX)→(X)→(I-B) is performed without isolation of the intermediates.

The reactions (VIII)→(IX)→(X)→(I-B) are preferably carried out without isolation of the intermediates.

Inert solvents for the process step (VI)+(VII)→(VIII) are, for example, alcohols such as methanol, ethanol, n-propanol, isopropanol, n-butanol or tert-butanol, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), pyridine or acetonitrile. It is also possible to use mixtures of the solvents mentioned. Preference is given to methanol or ethanol.

The reaction (VI)+(VII)→(VIII) is generally carried out in a temperature range of from +50° C. to +120° C., preferably from +50° C. to +100° C., optionally in a microwave. The reaction can be performed at atmospheric or elevated pressure (for example in the range from 0.5 to 5 bar). The reaction is generally carried out at atmospheric pressure.

Inert solvents for the process step (II)→(VI) are, for example, alcohols such as methanol, ethanol, n-propanol, isopropanol, n-butanol or tert-butanol, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), pyridine or acetonitrile. It is also possible to use mixtures of the solvents mentioned. Preference is given to ethanol.

Suitable bases for the process step (II)→(VI) are alkali metal hydroxides such as, for example, lithium hydroxide, sodium hydroxide or potassium hydroxide, alkali metal carbonates such as lithium carbonate, sodium carbonate, potassium carbonate or cesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to triethylamine.

The reaction (II)→(VI) is generally carried out in a temperature range of from 0° C. to +60° C., preferably from +10° C. to +30° C. The reaction can be performed at atmospheric or elevated pressure (for example in the range from 0.5 to 5 bar). The reaction is generally carried out at atmospheric pressure.

The preparation processes described can be illustrated by way of example by the following synthesis schemes (Schemes 1 and 2):

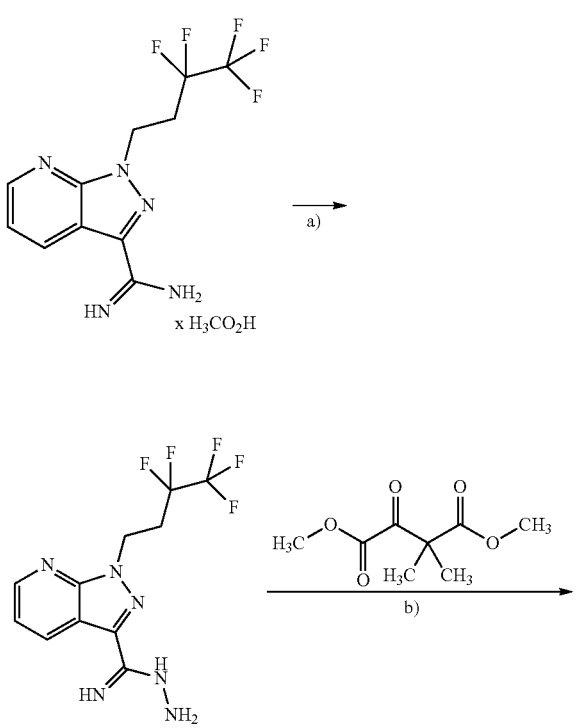

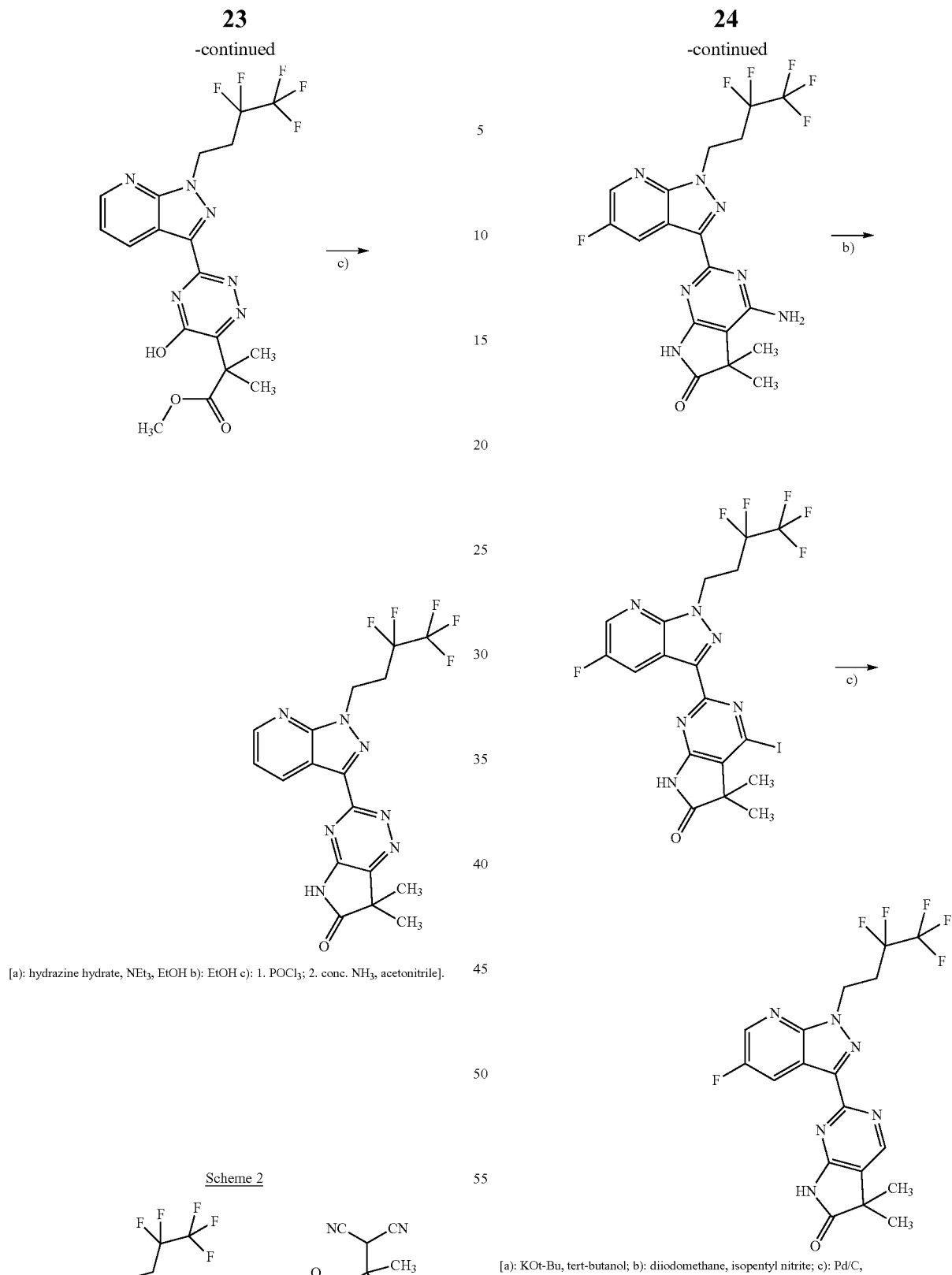

[a]: hydrazine hydrate, NEt₃, EtOH b): EtOH c): 1. POCl₃; 2. conc. NH₃, acetonitrile].

[a]: KOt-Bu, tert-butanol; b): diiodomethane, isopentyl nitrite; c): Pd/C, hydrogen, DMF].

In an alternative process, the preparation of the compounds of the formula (I) according to the invention can take place by reversing the order of the reaction steps using protective group chemistry, as shown by way of example in the synthesis scheme below (Scheme 6):

Scheme 6

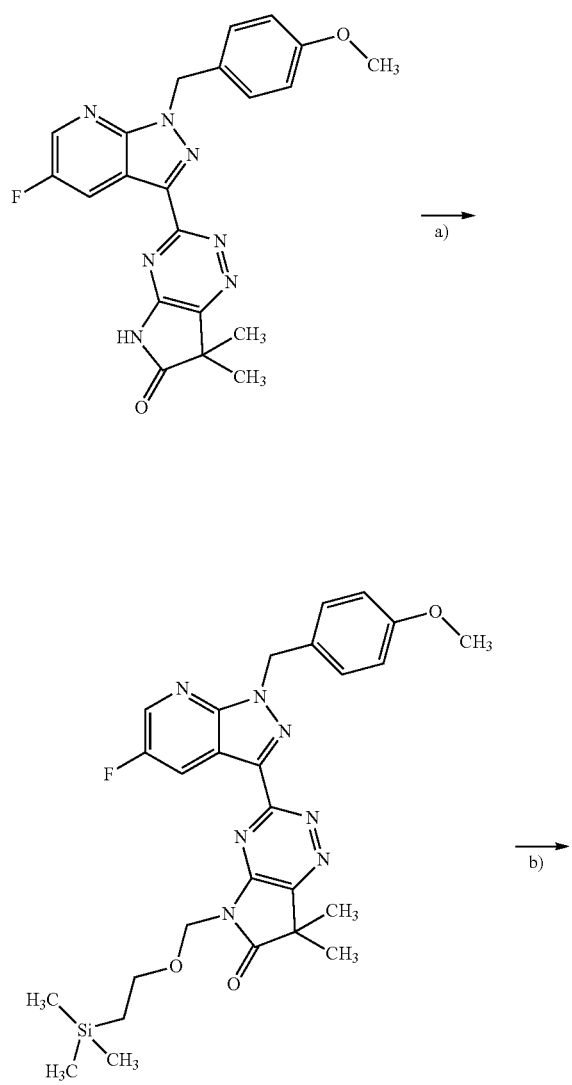

[a]: 2-(trimethylsilyl)ethoxymethyl chloride, $Cs_2CO_3$, DMF; b): ammonium cerium(IV) nitrate, acetonitrile, water; c): $Cs_2CO_3$, DMF; d): 1) TFA, dichloromethane, 2) HCl, ethanol].

Further compounds according to the invention can optionally also be prepared by conversions of functional groups of individual substituents, especially those listed for L and $R^3$, proceeding from compounds of the formula (I) obtained by above processes. These conversions are performed by customary methods known to those skilled in the art and include, for example, reactions such as nucleophilic and electrophilic substitutions, oxidations, reductions, hydrogenations, transition metal-catalyzed coupling reactions, eliminations, alkylation, amination, esterification, ester cleavage, etherification, ether cleavage, formation of carbonamides, and introduction and removal of temporary protecting groups.

The compounds of the formula (II) can be prepared by cyclizing a compound of the formula (XI)

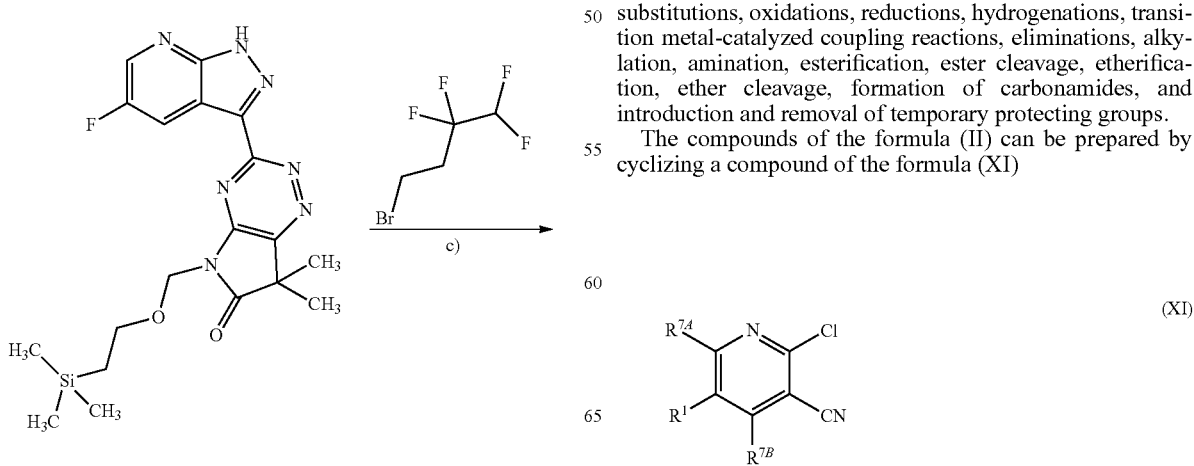

in which $R^1$, $R^{7A}$ and $R^{7B}$ each have the meanings given above, in an inert solvent with hydrazine hydrate to give the compound of the formula (XII)

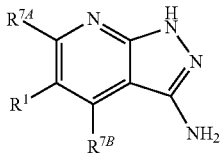
(XII)

in which $R^1$, $R^{7A}$ and $R^{7B}$ each have the meanings given above, then reacting the latter, in an inert solvent in the presence of a suitable Lewis acid, first with isopentyl nitrite to give the corresponding diazonium salt, and then converting the latter directly with sodium iodide into the compound of the formula (XIII)

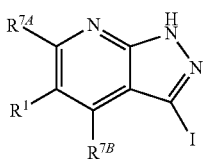
(XIII)

in which $R^1$, $R^{7A}$ and $R^{7B}$ each have the meanings given above, this is subsequently converted in an inert solvent in the presence of a suitable base with the compound of the formula (XIV)

$R^2—X^1$ (XIV)

in which $R^2$ has the meaning given above and
$X^1$ is a suitable leaving group, for example halogen, tosylate or mesylate, into a compound of the formula (XV)

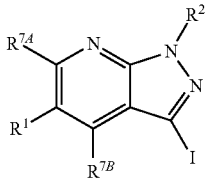
(XV)

in which $R^1$, $R^2$, $R^{7A}$ and $R^{7B}$ each have the meanings given above, this is then reacted in an inert solvent with copper cyanide to give a compound of the formula (XVI)

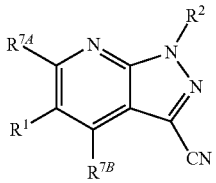
(XVI)

in which $R^1$, $R^2$, $R^{7A}$ and $R^{7B}$ each have the meanings given above, and this is finally reacted under acidic conditions with an ammonia equivalent.

Inert solvents for the process step (XI)→(XII) are alcohols such as methanol, ethanol, n-propanol, isopropanol, n-butanol, tert-butanol or 1,2-ethanediol, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), pyridine, acetonitrile or else water. It is also possible to use mixtures of the solvents mentioned. Preference is given to 1,2-ethanediol.

The reaction (XI)→(XII) is generally carried out in a temperature range of from +60° C. to +200° C., preferably at from +120° C. to +180° C. The reaction can be carried out at atmospheric, elevated or reduced pressure (for example from 0.5 to 5 bar). The reaction is generally carried out at atmospheric pressure.

Inert solvents for the reaction (XII)→(XIII) are, for example, halohydrocarbons such as dichloromethane, trichloromethane, tetrachloromethane, trichloroethylene or chlorobenzene, ethers such as diethyl ether, dioxane, tetrahydrofuran, glycol dimethyl ether or diethylene glycol dimethyl ether, or other solvents such as dimethylformamide (DMF), dimethyl sulfoxide (DMSO), N,N'-dimethylpropyleneurea (DMPU), N-methylpyrrolidone (NMP), pyridine or acetonitrile. Preference is given to DMF.

Suitable Lewis acids for the process step (XII)→(XIII) are boron trifluoride/diethyl ether complex, cerium(IV) ammonium nitrate (CAN), tin(II) chloride, lithium perchlorate, zinc (II) chloride, indium(III) chloride or indium(III) bromide. Preference is given to boron trifluoride/diethyl ether complex.

The reaction (XII)→(XIII) is generally carried out in a temperature range from −78° C. to +40° C., preferably at from 0° C. to +20° C. The reaction can be carried out at atmospheric, elevated or reduced pressure (for example from 0.5 to 5 bar). The reaction is generally carried out at atmospheric pressure.

Inert solvents for the reaction (XIII)+(XIV)→(XV) are, for example, halohydrocarbons such as dichloromethane, trichloromethane, tetrachloromethane, trichloroethylene or chlorobenzene, ethers such as diethyl ether, dioxane, tetrahydrofuran, glycol dimethyl ether or diethylene glycol dimethyl ether, or other solvents such as dimethylformamide (DMF), dimethyl sulfoxide (DMSO), N,N'-dimethylpropyleneurea (DMPU), N-methylpyrrolidone (NMP), pyridine, acetonitrile. Preference is given to DMF.

Suitable bases for the process step (XIII)+(XIV)→(XV) are alkali metal hydrides such as potassium hydride or sodium hydride, alkali metal carbonates such as lithium carbonate, sodium carbonate, potassium carbonate or cesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, amides such as sodium amide, lithium bis(trimethylsilyl)amide, sodium bis(trimethylsilyl)amide or potassium bis(trimethylsilyl) amide or lithium diisopropylamide, organometallic compounds such as butyllithium or phenyllithium, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to cesium carbonate.

The reaction (XIII)+(XIV)→(XV) is generally carried out in a temperature range of from 0° C. to +60° C., preferably at from +10° C. to +25° C. The reaction can be carried out at atmospheric, elevated or reduced pressure (for example from 0.5 to 5 bar). The reaction is generally carried out at atmospheric pressure.

Inert solvents for the process step (XV)→(XVI) are, for example, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulfoxide (DMSO), N,N'-dimethylpropyleneurea (DMPU), N-methylpyrrolidone (NMP), pyridine or acetonitrile. It is also possible to use mixtures of the solvents mentioned. Preference is given to DMSO.

The reaction (XV)→(XVI) is generally carried out in a temperature range of from +20° C. to +180° C., preferably at from +100° C. to +160° C., optionally in a microwave. The reaction can be carried out at atmospheric, elevated or reduced pressure (for example from 0.5 to 5 bar). The reaction is generally carried out at atmospheric pressure.

The reaction (XVI)→(II) is carried out using methods known to the person skilled in the art in a two-step process, initially with formation of the imino ester using sodium methoxide in methanol at 0° C. to +40° C. and then nucleophilic addition of an ammonia equivalent such as, for example, ammonia or ammonium chloride in a suitable acid with formation of the amidine (III) at +50 to +150° C.

Acids suitable for forming the amidine (II) are inorganic acids such as, for example, hydrogen chloride/hydrochloric acid, sulfuric acid, polyphosphoric acid or phosphoric acid, or organic acids such as, for example, acetic acid, trifluoroacetic acid or formic acid. Preference is given to using hydrochloric acid or acetic acid.

The preparation process described can be illustrated in an exemplary manner by the synthesis scheme below (Scheme 3):

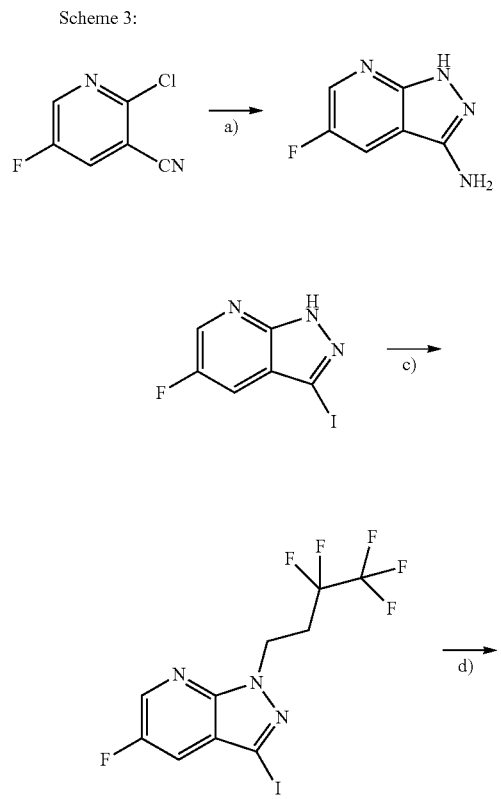

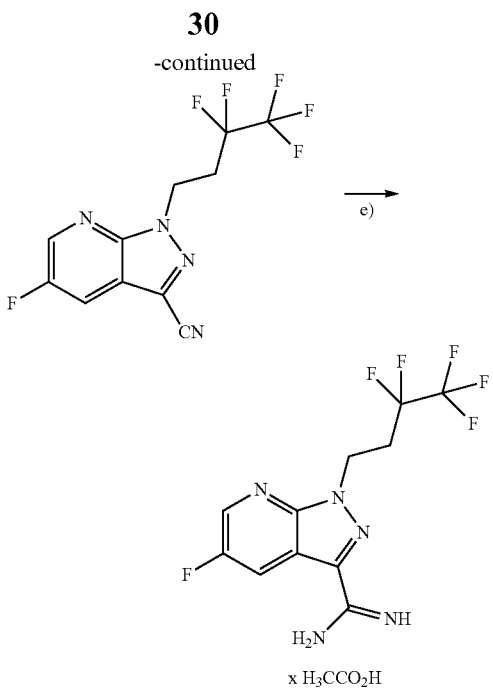

[a): hydrazine hydrate, 1,2-ethanediol; b): isopentyl nitrite, NaI, THF; b): 1,1,1,2,2-pentafluoro-4-iodobutane, Cs$_2$CO$_3$, DMF; d): CuCN, DMSO, e): 1. NaOMe, MeOH, 2. NH$_4$Cl, acetic acid].

Alternatively, the preparation of the compounds of the formula (II) is carried out as shown in the synthesis scheme below (Scheme 4):

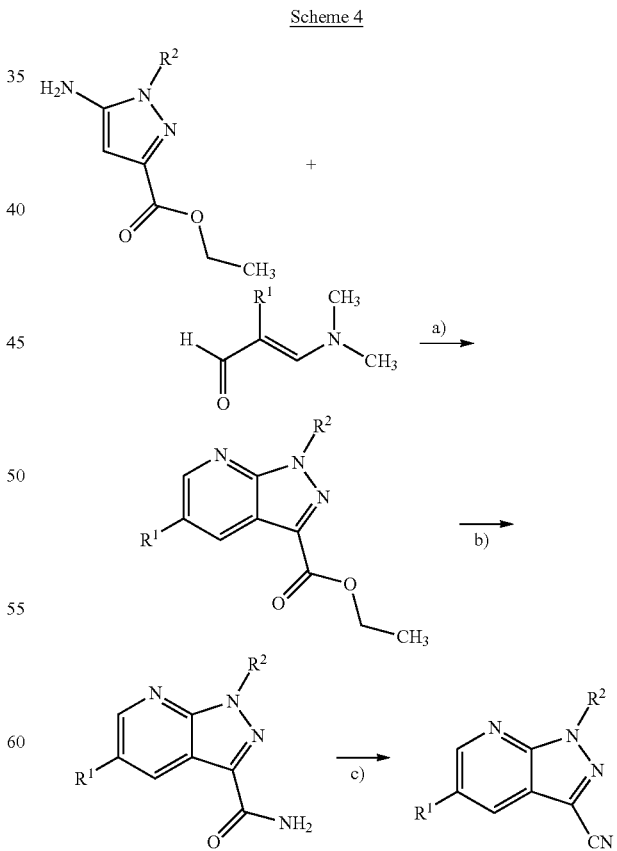

[a): TFA, dioxane; b) NH$_3$; c) trifluoroacetic anhydride].

The compound of the formula (XI) is known from the literature [cf., for example, Winn M., *J. Med. Chem.* 1993, 36, 2676-7688; EP 634 413-A1; CN 1613849-A; EP 1626045-A1; WO 2009/018415] or can be prepared analogously to processes known from the literature or as shown in the synthesis scheme below (Scheme 5):

Scheme 5:

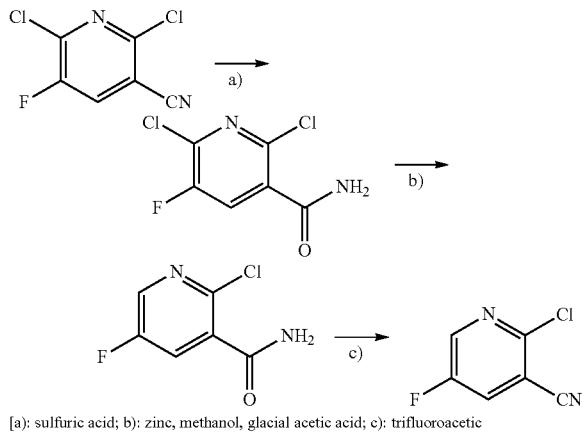

[a]: sulfuric acid; b): zinc, methanol, glacial acetic acid; c): trifluoroacetic anhydride, dichloromethane].

The compounds of the formulae (III) and (VII) are commercially available, known from the literature or can be prepared in analogy to processes known from the literature.

The compounds according to the invention act as potent stimulators of soluble guanylate cyclase and have an identical or improved therapeutic profile compared to compounds known from the prior art, such as, for example, with respect to their in vivo properties such as, for example, their pharmacokinetic and pharmacodynamic behavior and/or their dose-activity relationship and/or their safety profile. They are therefore suitable for the treatment and/or prophylaxis of diseases in man and animals.

The compounds according to the invention cause vasorelaxation and inhibition of platelet aggregation, and lead to a decrease in blood pressure and to a rise in coronary blood flow. These effects are mediated by a direct stimulation of soluble guanylate cyclase and an intracellular rise in cGMP. In addition, the compounds according to the invention enhance the action of substances which increase the cGMP level, for example EDRF (endothelium-derived relaxing factor), NO donors, protoporphyrin IX, arachidonic acid or phenylhydrazine derivatives.

The compounds according to the invention are suitable for the treatment and/or prophylaxis of cardiovascular, pulmonary, thromboembolic and fibrotic disorders.

The compounds according to the invention can therefore be used in medicaments for the treatment and/or prophylaxis of cardiovascular disorders, for example hypertension, acute and chronic heart failure, coronary heart disease, stable and unstable angina pectoris, peripheral and cardiovascular disorders, arrhythmias, atrial and ventricular arrhythmias and impaired conduction, for example atrioventricular grade I-III blocks (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, Sick-Sinus syndrome, syncopes, AV-nodal re-entry tachycardia, Wolff-Parkinson-White syndrome, acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for the treatment and/or prophylaxis of thromboembolic disorders and ischemias such as myocardial ischemia, myocardial infarction, stroke, cardiac hypertrophy, transient and ischemic attacks, preeclampsia, inflammatory cardiovascular disorders, spasms of the coronary arteries and peripheral arteries, edema formation, for example pulmonary edema, cerebral edema, renal edema or edema caused by heart failure, impaired peripheral perfusion, reperfusion damage, arterial and venous thromboses, microalbuminuria, myocardial insufficiency, endothelial dysfunction, for prevention of restenoses, such as after thrombolysis treatments, percutaneous transluminal angioplasties (PTA), transluminal coronary angioplasties (PTCA), heart transplants and bypass operations, and micro- and macrovascular damage (vasculitis), elevated levels of fibrinogen and of low-density LDL, and elevated concentrations of plasminogen activator inhibitor 1 (PAI-1), and for the treatment and/or prophylaxis of erectile dysfunction and female sexual dysfunction.

In the context of the present invention, the term "heart failure" also encompasses both acute and chronic forms of heart failure, and also more specific or related types of disease, such as acute decompensated heart failure, right heart failure, left heart failure, global failure, ischemic cardiomyopathy, dilated cardiomyopathy, hypertrophic cardiomyopathy, idiopathic cardiomyopathy, congenital heart defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, diastolic heart failure and systolic heart failure, and acute phases of worsening of existing chronic heart failure (worsening heart failure).

In addition, the compounds according to the invention can also be used for the treatment and/or prophylaxis of arteriosclerosis, impaired lipid metabolism, hypolipoproteinemias, dyslipidemias, hypertriglyceridemias, hyperlipidemias, hypercholesterolemias, abetalipoproteinemia, sitosterolemia, xanthomatosis, Tangier disease, adiposity, obesity and of combined hyperlipidemias and metabolic syndrome.

Moreover, the compounds according to the invention can be used for the treatment and/or prophylaxis of primary and secondary Raynaud's phenomenon, of microcirculation disorders, claudication, peripheral and autonomic neuropathies, diabetic microangiopathies, diabetic retinopathy, diabetic ulcers at the extremities, gangrene, CREST syndrome, erythematosis, onychomycosis, rheumatic disorders, and for promotion of wound healing.

The compounds according to the invention are furthermore suitable for treating urological disorders such as, for example, benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic over-active bladder (OAB) and (IC), incontinence (UI) such as, for example, mixed urinary incontinence, urge urinary incontinence, stress urinary incontinence or overflow urinary incontinence (MUI, UUI, SUI, OUI), pelvic pain, benign and malignant disorders of the organs of the male and female urogenital system.

The compounds according to the invention are furthermore suitable for the treatment and/or prophylaxis of kidney disorders, in particular of acute and chronic renal insufficiency and acute and chronic renal failure. In the context of the present invention, the term "renal insufficiency" encompasses both acute and chronic manifestations of renal insufficiency, and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example, by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphatemia and/or need for dialysis. The present invention also encompasses the use of the compounds according to the invention for the treatment and/or prophylaxis of sequelae of renal insufficiency, for example pulmonary edema, heart failure, uremia, anemia, electrolyte disturbances (for example hypercalemia, hyponatremia) and disturbances in bone and carbohydrate metabolism.

Furthermore, the compounds according to the invention are also suitable for the treatment and/or prophylaxis of asthmatic disorders, pulmonary arterial hypertension (PAH) and other forms of pulmonary hypertension (PH) including pulmonary hypertension associated with left heart disease, HIV, sickle cell anemia, thromboembolisms (CTEPH), sarcoidosis, COPD or pulmonary fibrosis, or chronic-obstructive pulmonary disease (COPD), acute respiratory distress syndrome (ARDS), acute lung injury (ALI), alpha-1 antitrypsin deficiency (AATD), pulmonary fibrosis, pulmonary emphysema (for example pulmonary emphysema induced by cigarette smoke) and cystic fibrosis (CF).

The compounds described in the present invention are also active ingredients for control of central nervous system disorders characterized by disturbances of the NO/cGMP system. More particularly, they are suitable for improving perception, concentration, learning or memory after cognitive impairments such as those occurring particularly in the event of situations/diseases/syndromes such as mild cognitive impairment, age-associated learning and memory impairments, age-associated memory losses, vascular dementia, craniocerebral trauma, stroke, dementia occurring after strokes (post-stroke dementia), post-traumatic craniocerebral trauma, general concentration impairments, concentration impairments in children having learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelination, multiple sclerosis, thalamic degeneration, Creutzfeld-Jacob dementia, HIV dementia, schizophrenia with dementia or Korsakoff's psychosis. They are also suitable for the treatment and/or prophylaxis of central nervous system disorders such as states of anxiety, tension and depression, CNS-related sexual dysfunction and disrupted sleep, and for control of pathological disturbances of the intake of food, stimulants and addictive substances.

Furthermore, the compounds according to the invention are also suitable for regulating cerebral blood flow and are thus effective agents for control of migraine. They are also suitable for prophylaxis and control of sequelae of cerebral infarct (cerebral apoplexy) such as stroke, cerebral ischemia and skull-brain trauma. The compounds according to the invention can likewise be employed for controlling states of pain and tinnitus.

In addition, the compounds according to the invention have antiinflammatory action and can therefore be used as antiinflammatory agents for the treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin diseases and inflammatory eye diseases.

Furthermore, the compounds according to the invention can also be used for the treatment and/or prophylaxis of autoimmune diseases.

Furthermore, the compounds according to the invention are suitable for the treatment and/or prophylaxis of fibrotic disorders of the internal organs, for example of the lung, of the heart, of the kidney, of the bone marrow and especially of the liver, and also of dermatological fibroses and fibrotic disorders of the eye. In the context of the present inventions, the term "fibrotic disorders" encompasses especially the following terms: hepatic fibrosis, hepatic cirrhosis, pulmonary fibrosis, endomyocardial fibrosis, nephropathy, glomerulonephritis, interstitial renal fibrosis, fibrotic damage resulting from diabetes, myelofibrosis and similar fibrotic disorders, scleroderma, morphea, keloids, hypertrophic scarring (including after surgical interventions), naevi, diabetic retinopathy, proliferative vitreoretinopathy and disorders of the connective tissue (for example sarcoidosis).

Furthermore, the compounds according to the invention are suitable for control of postoperative scarring, for example resulting from glaucoma operations.

The compounds according to the invention can also be used cosmetically for aging and keratinized skin.

Moreover, the compounds according to the invention are suitable for the treatment and/or prophylaxis of hepatitis, neoplasms, osteoporosis, glaucoma and gastroparesis.

The present invention further provides for the use of the compounds according to the invention for the treatment and/or prophylaxis of disorders, in particular the disorders mentioned above.

The present invention further provides for the use of the compounds according to the invention for the treatment and/or prophylaxis of heart failure, angina pectoris, hypertension, pulmonary hypertension, ischemias, vascular disorders, renal insufficiency, thromboembolic disorders, fibrotic disorders and arteriosclerosis.

The present invention further provides the compounds according to the invention for use in a method for the treatment and/or prophylaxis of heart failure, angina pectoris, hypertension, pulmonary hypertension, ischemias, vascular disorders, renal insufficiency, thromboembolic disorders, fibrotic disorders and arteriosclerosis.

The present invention further provides for the use of the compounds according to the invention for production of a medicament for the treatment and/or prophylaxis of disorders, especially of the aforementioned disorders.

The present invention further provides for the use of the compounds according to the invention for production of a medicament for the treatment and/or prophylaxis of heart failure, angina pectoris, hypertension, pulmonary hypertension, ischemias, vascular disorders, renal insuffuciency, thromboembolic disorders, fibrotic disorders and arteriosclerosis.

The present invention further provides a method for the treatment and/or prophylaxis of disorders, in particular the disorders mentioned above, using an effective amount of at least one of the compounds according to the invention.

The present invention further provides a method for the treatment and/or prophylaxis of heart failure, angina pectoris, hypertension, pulmonary hypertension, ischemias, vascular disorders, renal insufficiency, thromboembolic disorders, fibrotic disorders and arteriosclerosis using an effective amount of at least one of the compounds according to the invention.

The compounds according to the invention can be used alone or, if required, in combination with other active compounds. The present invention further provides medicaments comprising at least one of the compounds according to the invention and one or more further active compounds, especially for the treatment and/or prophylaxis of the aforementioned disorders. Preferred examples of suitable active compound combinations include:

- organic nitrates and NO donors, for example sodium nitroprusside, nitroglycerine, isosorbide mononitrate, isosorbide dinitrate, molsidomine or SIN-1, and inhaled NO;
- compounds which inhibit the breakdown of cyclic guanosine monophosphate (cGMP), for example inhibitors of phosphodiesterases (PDE) 1, 2 and/or 5, especially PDE 5 inhibitors such as sildenafil, vardenafil and tadalafil;
- antithrombotic agents, by way of example and with preference from the group of the platelet aggregation inhibitors, the anticoagulants or the profibrinolytic substances;
- hypotensive active compounds, by way of example and with preference from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics; and/or
- active compounds which modify lipid metabolism, by way of example and with preference from the group of thyroid receptor agonists, cholesterol synthesis inhibitors such as, by way of example and with preference, HMG-CoA reductase inhibitors or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Antithrombotic agents are preferably understood to mean compounds from the group of the platelet aggregation inhibitors, the anticoagulants or the profibrinolytic substances.

In a preferred embodiment of the invention, the compounds according to the invention are administered in combination with a platelet aggregation inhibitor, by way of example and with preference aspirin, clopidogrel, ticlopidin or dipyridamole.

In a preferred embodiment of the invention, the compounds according to the invention are administered in combination with a thrombin inhibitor, by way of example and with preference ximelagatran, melagatran, bivalirudin or clexane.

In a preferred embodiment of the invention, the compounds according to the invention are administered in combination with a GPIIb/IIIa antagonist such as, by way of example and with preference, tirofiban or abciximab.

In a preferred embodiment of the invention, the compounds according to the invention are administered in combination with a factor Xa inhibitor, by way of example and with preference rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist, by way of example and with preference coumarin.

Hypotensive agents are preferably understood to mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds according to the invention are administered in combination with a calcium antagonist, by way of example and with preference nifedipine, amlodipine, verapamil or diltiazem.

In a preferred embodiment of the invention, the compounds according to the invention are administered in combination with an alpha-1-receptor blocker, by way of example and with preference prazosin.

In a preferred embodiment of the invention, the compounds according to the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, by way of example and with preference losartan, candesartan, valsartan, telmisartan or embusartan.

In a preferred embodiment of the invention, the compounds according to the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds according to the invention are administered in combination with an endothelin antagonist, by way of example and with preference bosentan, darusentan, ambrisentan or sitaxsentan.

In a preferred embodiment of the invention, the compounds according to the invention are administered in combination with a renin inhibitor, by way of example and with preference aliskiren, SPP-600 or SPP-800.

In a preferred embodiment of the invention, the compounds according to the invention are administered in combination with a mineralocorticoid receptor antagonist, by way of example and with preference spironolactone or eplerenone.

In a preferred embodiment of the invention, the compounds according to the invention are administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein (a) antagonists.

In a preferred embodiment of the invention, the compounds according to the invention are administered in combination with a CETP inhibitor, by way of example and with preference dalcetrapib, BAY 60-5521, anacetrapib oder CETP vaccine (CETi-1).

In a preferred embodiment of the invention, the compounds according to the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, by way of example and with preference BMS-188494 or TAK-475.

In a preferred embodiment of the invention, the compounds according to the invention are administered in combination with an ACAT inhibitor, by way of example and with preference avasimibe, melinamide, pactimibe, eflucimibe or SMP-797.

In a preferred embodiment of the invention, the compounds according to the invention are administered in combination with an MTP inhibitor, by way of example and with preference implitapide, BMS-201038, R-103757 or JTT-130.

In a preferred embodiment of the invention, the compounds according to the invention are administered in combination with a PPAR-gamma agonist, by way of example and with preference pioglitazone or rosiglitazone.

In a preferred embodiment of the invention, the compounds according to the invention are administered in combination with a PPAR-delta agonist, by way of example and with preference GW 501516 or BAY 68-5042.

In a preferred embodiment of the invention, the compounds according to the invention are administered in combination with a cholesterol absorption inhibitor, by way of example and with preference ezetimibe, tiqueside or pamaqueside.

In a preferred embodiment of the invention, the compounds according to the invention are administered in combination with a lipase inhibitor, by way of example and with preference orlistat.

In a preferred embodiment of the invention, the compounds according to the invention are administered in combination with a polymeric bile acid adsorbent, by way of example and with preference cholestyramine, colestipol, colesolvam, CholestaGel or colestimide.

In a preferred embodiment of the invention, the compounds according to the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds according to the invention are administered in combination with a lipoprotein (a) antagonist, by way of example and with preference gemcabene calcium (CI-1027) or nicotinic acid.

The present invention further provides medicaments which comprise at least one compound according to the invention, typically together with one or more inert nontoxic pharmaceutically suitable auxiliaries, and for the use thereof for the aforementioned purposes.

The compounds according to the invention may act systemically and/or locally. For this purpose, they can be administered in a suitable manner, for example by the oral, parenteral, pulmonal, nasal, sublingual, lingual, buccal, rectal, dermal, transdermal, conjunctival, otic route, or as an implant or stent.

The compounds according to the invention can be administered in administration forms suitable for these administration routes.

Suitable administration forms for oral administration are those which work according to the prior art, which release the compounds according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the inventive compound), tablets or films/oblates which disintegrate rapidly in the oral cavity, films/lyophilizates or capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardiac, intraspinal or intralumbar route) or with inclusion of an absorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The compounds according to the invention can be converted to the administration forms mentioned. This can be accomplished in a manner known per se by mixing with inert nontoxic pharmaceutically suitable auxiliaries. These auxiliaries include carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavor and/or odor correctors.

In general, it has been found to be advantageous in the case of parenteral administration to administer amounts of from about 0.001 to 1 mg/kg, preferably about 0.01 to 0.5 mg/kg, of body weight to achieve effective results. In the case of oral administration, the dose is about 0.001 to 2 mg/kg, preferably about 0.001 to 1 mg/kg, of body weight.

It may nevertheless be necessary where appropriate to deviate from the stated amounts, specifically as a function of the body weight, route of administration, individual response to the active compound, nature of the preparation and time or interval over which administration takes place. For instance, in some cases, less than the aforementioned minimum amount may be sufficient, while in other cases the upper limit mentioned must be exceeded. In the case of administration of relatively large amounts, it may be advisable to divide these into several individual doses over the course of the day.

The working examples which follow illustrate the invention. The invention is not restricted to the examples.

The percentages in the tests and examples which follow are, unless stated otherwise, percentages by weight; parts are parts by weight. Solvent ratios, dilution ratios and concentration figures for liquid/liquid solutions are each based on volume.

A. EXAMPLES

Abbreviations and Acronyms:
aq. aqueous solution
calc. calculated
DCI direct chemical ionization (in MS)
DMF dimethylformamide
DMSO dimethyl sulfoxide
eq. equivalent(s)
ESI electrospray ionization (in MS)
Et ethyl
h hour(s)
HPLC high-pressure, high-performance liquid chromatography
HRMS high-resolution mass spectrometry
conc. concentrated
LC/MS liquid chromatography-coupled mass spectrometry
LiHMDS lithium hexamethyldisilazide
Me methyl
min minute(s)
MS mass spectrometry
NMR nuclear magnetic resonance spectrometry
Pd$_2$dba$_3$ tris(dibenzylideneacetone)dipalladium
Ph phenyl
RT room temperature
R$_t$ retention time (in HPLC)
THF tetrahydrofuran
UV ultraviolet spectrometry
v/v ratio by volume (of a solution)
LC/MS Methods:
Method 1 (LC-MS):
Instrument: Waters Acquity SQD UPLC System; column: Waters Acquity UPLC HSS T3 1.8μ 30×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.60 ml/min; UV detection: 208-400 nm.
Method 2 (LC-MS):
Instrument: Waters Acquity SQD UPLC System; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.
Method 3 (LC-MS):
Instrument: Micromass Quattro Premier with Waters UPLC Acquity; column: Thermo Hypersil GOLD 1.9μ 50×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A; oven: 50° C.; flow rate: 0.3 ml/min; UV detection: 210 nm.
Starting Materials and Intermediates:

Example 1A

5-Fluoro-3-iodo-1H-pyrazolo[3,4-b]pyridine

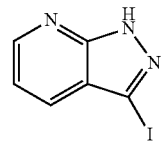

The synthesis is described in in WO 2006/130673, Example 4.

Example 2A 2,6-Dichloro-5-fluoronicotinamide

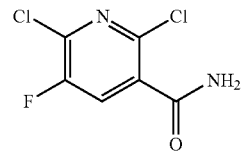

A suspension of 25 g (130.90 mmol) of 2,6-dichloro-5-fluoro-3-cyanopyridine in conc. sulfuric acid (125 ml) was stirred at 60-65° C. for 1 h. After cooling to RT, the contents of the flask were poured onto ice-water and extracted three times with ethyl acetate (100 ml each time). The combined organic phases were washed with water (100 ml) and then with saturated aqueous sodium bicarbonate solution (100 ml), dried and concentrated on a rotary evaporator. The material obtained was dried under high vacuum.

Yield: 24.5 g (90% of theory)
$^1$H NMR (400 MHz, DMSO-d$_6$): δ=7.95 (br s, 1H), 8.11 (br s, 1H), 8.24 (d, 1H).

Example 3A

2-Chloro-5-fluoronicotinamide

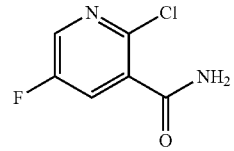

At RT, 44 g (210.58 mmol) of 2,6-dichloro-5-fluoronicotinamide were added to a suspension of 21.9 g (335.35 mmol) of zinc in methanol (207 ml). Acetic acid (18.5 ml) was then added, and the mixture was heated at reflux with stirring for 24 h. The contents of the flask were then decanted off from the zinc, and ethyl acetate (414 ml) and saturated aqueous sodium bicarbonate solution (414 ml) were added, followed by extraction with vigorous stirring. Subsequently, the reaction mixture was filtered with suction through kieselguhr, and the filter cake was washed three times with ethyl acetate (517 ml each time). The organic phase was removed and the aqueous phase was washed with ethyl acetate (258 ml). The combined organic phases were washed once with saturated aqueous sodium bicarbonate solution (414 ml), dried and concentrated under reduced pressure. Dichloromethane (388 ml) was added to the solid obtained in this manner, and extraction was effected by stirring for 20 min. The mixture was once more filtered off with suction, and the filter cake was washed with diethyl ether and sucked dry.

Yield: 20.2 g (53% of theory)

$^1$H NMR (400 MHz, DMSO-$d_6$): δ=7.87 (br s, 1H), 7.99 (dd, 1H), 8.10 (br s, 1H), 8.52 (d, 1H).

Example 4A

2-Chloro-5-fluoronicotinonitrile

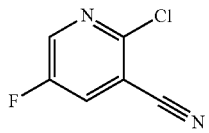

81.2 ml (582.25 mmol) of triethylamine were added to a suspension of 46.2 g (264.66 mmol) of 2-chloro-5-fluoronicotinamide in dichloromethane (783 ml), and the mixture was cooled to 0° C. With stirring, 41.12 ml (291.13 mmol) of trifluoroacetic anhydride were then slowly added dropwise, and the mixture was stirred at 0° C. for 1.5 h. The reaction solution was subsequently washed twice with saturated aqueous sodium bicarbonate solution (391 ml each time), dried and concentrated under reduced pressure.

Yield: 42.1 g (90% of theory)

$^1$H NMR (400 MHz, DMSO-$d_6$): δ=8.66 (dd, 1H), 8.82 (d, 1H).

Example 5A

5-Fluoro-1H-pyrazolo[3,4-b]pyridine-3-amine

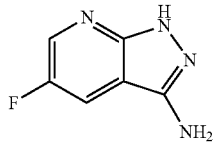

A suspension of 38.5 g (245.93 mmol) of 2-chloro-5-fluoronicotinonitrile was initially charged in 1,2-ethanediol (380 ml), and hydrazine hydrate (119.6 ml) was then added. With stirring, the mixture was heated at reflux for 4 h. Cooling resulted in the precipitation of a solid, which was admixed with water (380 ml) and extracted by stirring at RT for 10 min. The suspension was then filtered with suction through a frit, and the filter cake was washed with water (200 ml) and with THF at −10° C. (200 ml). The solid was dried under high vacuum over phosphorus pentoxide.

Yield: 22.8 g (61% of theory)

$^1$H NMR (400 MHz, DMSO-$d_6$): δ=5.54 (s, 2H), 7.96 (dd, 1H), 8.38 (m, 1H), 12.07 (m, 1H).

Example 6A

5-Fluoro-3-iodo-1H-pyrazolo[3,4-b]pyridine

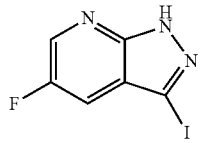

10 g (65.75 mmol) of 5-fluoro-1H-pyrazolo[3,4-b]pyridine-3-amine were initially charged in THF (329 ml), and the mixture was cooled to 0° C. 16.65 ml (131.46 mmol) of boron trifluoride/diethyl ether complex were then added slowly. The reaction mixture was cooled further to −10° C. A solution of 10.01 g (85.45 mmol) of isopentyl nitrite in THF (24.39 ml) was then added slowly, and the mixture was stirred for a further 30 min. The reaction mixture was diluted with cold diethyl ether (329 ml) and the resulting solid was filtered off. The diazonium salt thus prepared was added a little at a time to a solution at 0° C. of 12.81 g (85.45 mmol) of sodium iodide in acetone (329 ml), and the mixture was stirred at RT for 30 min. The reaction mixture was poured onto ice-water (1.8 l) and extracted twice with ethyl acetate (487 ml each time). The collected organic phases were washed with saturated aqueous sodium chloride solution (244 ml), dried, filtered and concentrated. This gave 12.1 g (86% purity, 60% of theory) of the title compound as a solid.

LC-MS (Method 2): $R_t$=1.68 min
MS (ESIpos): m/z=264 (M+H)$^+$

Example 7A

5-Fluoro-3-iodo-1-(3,3,4,4,4-pentafluorobutyl)-1H-pyrazolo[3,4-b]pyridine

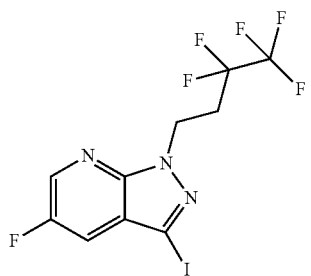 [SMILES: Fc1cnc2c(c1)c(I)nn2CCC(F)(F)C(F)(F)F]

5.0 g (19.010 mmol) of 5-fluoro-3-iodo-1H-pyrazolo[3,4-b]pyridine were initially charged in DMF (100 ml), and then 20.83 g (76.042 mmol) of 1,1,1,2,2-pentafluoro-4-iodobutane, and also 14.86 g (45.65 mmol) of cesium carbonate and 0.63 g (3.802 mmol) of potassium iodide were added. The mixture was stirred at 140° C. overnight. The mixture was then cooled and combined with a prior experiment which had been carried out analogously using 200 mg of 5-fluoro-3-iodo-1H-pyrazolo[3,4-b]pyridine. Solids were filtered off with suction and washed with DMF, and then the filtrate was concentrated under high vacuum. The residue was purified by means of preparative HPLC (methanol:water gradient). This gave 4.34 g (52% of theory) of the title compound.

LC-MS (Method 1): $R_t$=1.30 min
MS (ESIpos): m/z=410 (M-FH)+

¹H NMR (400 MHz, DMSO-d₆): δ=2.84-3.00 (m, 2H), 4.79 (t, 2H), 7.93 (dd, 1H), 8.71 (dd, 1H).

Example 8A

5-Fluoro-1-(3,3,4,4,4-pentafluorobutyl)-1H-pyrazolo[3,4-b]pyridine-3-carbonitrile

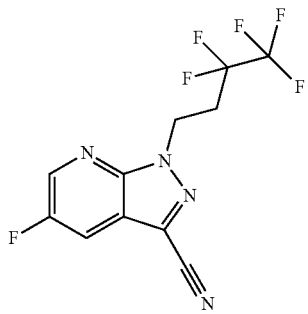 [SMILES: N#Cc1nn(CCC(F)(F)C(F)(F)F)c2ncc(F)cc12]

A suspension of 4.34 g (10.609 mmol) of example 7A and 1.045 g (11.670 mmol) of copper(I) cyanide was initially charged in DMSO (30 ml) and stirred at 150° C. for 2 h. After cooling, the mixture was filtered through Celite, the filter cake was washed with ethyl acetate and THF and the filtrate was then extracted four times with a solution of saturated aqueous ammonium chloride solution and conc. aqueous ammonia (3:1 v/v). The combined organic phases were washed with saturated aqueous sodium chloride solution, dried over sodium sulfate, filtered and concentrated under reduced pressure.

Yield: 3.19 g (97% of theory)
¹H NMR (400 MHz, DMSO-d₆): δ=2.94-3.09 (m, 2H), 4.93 (t, 2H), 8.54 (dd, 1H), 8.88 (dd, 1H).

Example 9A

5-Fluoro-1-(3,3,4,4,4-pentafluorobutyl)-1H-pyrazolo[3,4-b]pyridine-3-carboximidamide acetate

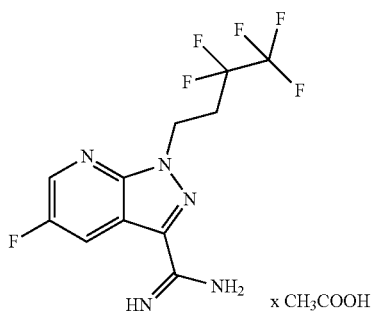 [SMILES: N=C(N)c1nn(CCC(F)(F)C(F)(F)F)c2ncc(F)cc12]

3.19 g (10.351 mmol) of Example 8A were added to 0.559 g (10.351 mmol) of sodium methoxide in methanol (25 ml), and the mixture was stirred at RT for 2 h. Thereafter, 0.664 g (12.421 mmol) of ammonium chloride and acetic acid (2.31 ml) were added and the mixture was heated to reflux overnight. Thereafter, the mixture was concentrated to dryness and the residue was admixed with ethyl acetate and 1N sodium hydroxide solution. The phases were separated. The aqueous phase was extracted once again with ethyl acetate. The combined organic phases were combined and concentrated. The crude product was reacted further without further purification.

Yield: 2.67 g (37% of theory, approx. 56% purity)
LC-MS (Method 2): R$_t$=0.68 min
MS (ESIpos): m/z=326 (M+H)⁺

Example 10A

Methyl 3,3-dicyano-2,2-dimethylpropanoate

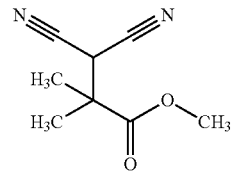

In THF (91 ml), 3 g (45.411 mmol) of malononitrile were added slowly to 1.816 g (45.411 mmol) of sodium hydride (60% in mineral oil). Subsequently, 5.876 ml (45.411 mmol) of methyl 2-bromo-2-methylpropanoate were added and the mixture was stirred at RT overnight. Thereafter, another 5.876 ml (45.411 mmol) of methyl 2-bromo-2-methylpropanoate were added and the mixture was heated at 50° C. overnight. Then yet another 1.762 ml (13.623 mmol) of methyl 2-bromo-2-methylpropanoate were added and the mixture was heated at 50° C. for a further 4 h. Saturated aqueous sodium bicarbonate solution was then added to the reaction, and the mixture was extracted three times with ethyl acetate. The combined organic phases were washed with saturated aqueous sodium chloride solution, dried over sodium sulfate, filtered and concentrated to dryness. This gave 8.9 g of crude product, which was purified by chromatography on silica gel (cyclohexane-ethyl acetate 4:1).

Yield: 6.47 g (85% of theory)
¹H NMR (400 MHz, DMSO-d₆): δ [ppm]=1.40 (s, 6H), 3.74 (s, 3H), 5.27 (s, 1H).

Example 11A

3-Iodo-1-(3,3,4,4,4-pentafluorobutyl)-1H-pyrazolo[3,4-b]pyridine

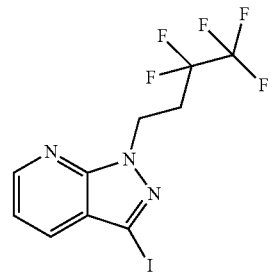 [SMILES: FC(F)(F)C(F)(F)CCn1nc(I)c2cccnc21]

10.00 g (40.813 mmol) of Example 1A were initially charged in DMF (170 ml), and then 12.30 g (44.894 mmol) of 1,1,1,2,2-pentafluoro-4-iodobutane in DMF (30 ml) and 14.628 g (44.894 mmol) of cesium carbonate were added. The mixture was stirred at RT for 2 days. Subsequently, another 12.30 g (44.894 mmol) of 1,1,1,2,2-pentafluoro-4-iodobutane and 14.628 g (44.894 mmol) of cesium carbonate were added and the mixture was stirred at RT for 2 days. Thereafter, 3.485 g (12.720 mmol) of 1,1,1,2,2-pentafluoro-4-iodobutane and 4.145 g (12.720 mmol) of cesium carbonate were added and the mixture was stirred at RT overnight. After this period, 5.00 g (18.250 mmol) of 1,1,1,2,2-pentafluoro-4-iodobutane and 5.946 g (18.250 mmol) of cesium carbonate were added and the mixture was stirred at room temperature for 6 days. The mixture was then stirred at 70° C. for 2 days. Solids were filtered off with suction and washed with DMF, and then the liquid was concentrated under high vacuum. The residue was purified by preparative HPLC (methanol:water (with 0.1% formic acid) gradient). This gave 5.48 g (34% of theory) of the title compound.

LC-MS (Method 1): $R_t$=1.23 min

MS (ESIpos): m/z=392 (M+H)$^+$ $^1$H NMR (400 MHz, DMSO-d$_6$): δ=2.87-3.00 (m, 2H), 4.81 (t, 2H), 7.33 (dd, 1H), 7.97 (dd, 1H), 8.65 (dd, 1H).

Example 12A 1-(3,3,4,4,4-Pentafluorobutyl)-1H-pyrazolo[3,4-b]pyridine-3-carbonitrile

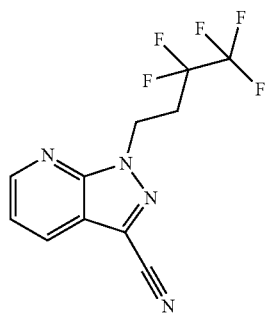 [SMILES: N#Cc1nn(CCC(F)(F)C(F)(F)F)c2ncccc12]

A suspension of 5.480 g (14.012 mmol) of Example 11A and 1.380 g (15.414 mmol) of copper(I) cyanide was initially charged in DMSO (50 ml) and stirred at 150° C. for 3 h. After cooling, the mixture was filtered through Celite and the filter cake was washed with ethyl acetate and THF. This was followed by washing four times with a solution of saturated aqueous ammonium chloride solution and conc. aqueous ammonia (3:1, v/v) and then with saturated aqueous sodium chloride solution. The organic phase was dried over sodium sulfate, filtered and concentrated, and then dried under high vacuum.

Yield: 3.59 g (88% of theory)

LC-MS (Method 2): $R_t$=1.04 min

MS (ESIpos): m/z=291 (M+H)$^+$ $^1$H NMR (400 MHz, DMSO-d$_6$): δ=2.97-3.10 (m, 2H), 4.94 (t, 2H), 7.55 (dd, 1H), 8.51 (dd, 1H), 8.81 (dd, 1H).

Example 13A 1-(3,3,4,4,4-Pentafluorobutyl)-1H-pyrazolo[3,4-b]pyridine-3-carboximidamide acetate

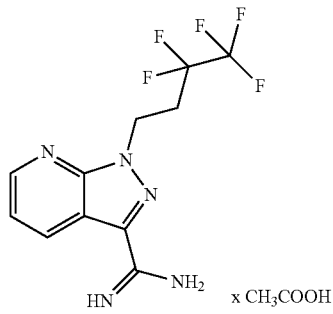 [SMILES: N=C(N)c1nn(CCC(F)(F)C(F)(F)F)c2ncccc12]

3.59 g (12.371 mmol) of Example 12A in methanol (20 ml) were added to 0.668 g (12.371 mmol) of sodium methoxide in methanol (40 ml), and the mixture was stirred at RT for 2 h. 0.794 g (14.845 mmol) of ammonium chloride and acetic acid (2.762 ml) were then added, and the mixture was heated to reflux overnight. Thereafter, the mixture was concentrated to dryness and the residue was admixed with ethyl acetate and 1N sodium hydroxide solution. The mixture was stirred vigorously at RT for about 1 h. The resulting solid was filtered off with suction and washed with ethyl acetate and water. The residue under high vacuum dried. This gave 0.507 g of product (11% of theory). The phases of the combined filtrates were separated and the aqueous phase was extracted twice with ethyl acetate. The combined organic phases were washed with water and saturated aqueous sodium chloride solution, dried over sodium sulfate, filtered and concentrated, and then dried under high vacuum. This gave a further 2.76 g (43% of theory, purity about 70%).

LC-MS (Method 2): $R_t$=0.58 min

MS (ESIpos): m/z=308 (M+H)$^+$ $^1$H NMR (400 MHz, DMSO-d$_6$): δ=1.84 (s, 3H), 2.95-3.08 (m, 2H), 4.85 (t, 2H), 7.39 (dd, 1H), 8.63-8.67 (m, 2H).

Example 14A 1-(3,3,4,4,4-Pentafluorobutyl)-1H-pyrazolo[3,4-b]pyridine-3-carboximidohydrazide

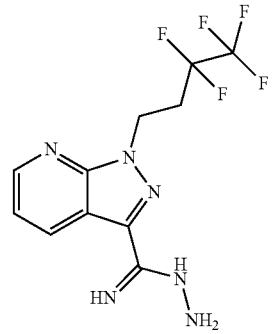 [SMILES: N=C(NN)c1nn(CCC(F)(F)C(F)(F)F)c2ncccc12]

0.6 g (about 1.144 mmol) of the compound from Example 13A were dissolved in ml of ethanol, and 462 mg (4.574 mmol) of triethylamine and 71 mg (1.144 mmol) of hydrazine hydrate (80% strength solution in water) were added at 0° C. The mixture was stirred at RT overnight and then concentrated on a rotary evaporator. This gave 689 mg (purity about 60%) of the title compound.

LC-MS (Method 2): $R_t$=0.57 min; MS (ESIpos): m/z=323 (M+H)+

Example 15A

5-Fluoro-1-(3,3,4,4,4-pentafluorobutyl)-1H-pyrazolo[3,4-b]pyridine-3-carboximidohydrazide

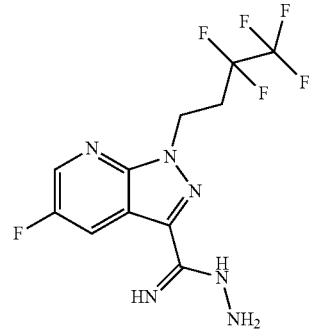 [SMILES: N=C(NN)c1nn(CCC(F)(F)C(F)(F)F)c2ncc(F)cc12]

0.62 g (0.901 mmol) of the compound from Example 9A (purity about 56%) were dissolved in 10.3 ml of ethanol, and 456 mg (4.506 mmol) of triethylamine and 70 mg (1.126 mmol) of hydrazine hydrate (80% strength solution in water) were added at 0° C. The mixture was stirred at RT overnight and then concentrated on a rotary evaporator. This gave a crude compound which was directly reacted further.

LC-MS (Method 1): $R_t$=0.61 min; MS (ESIpos): m/z=341 (M+H)+

Example 16A

Methyl 2-{5-hydroxy-3-[1-(3,3,4,4,4-pentafluorobutyl)-1H-pyrazolo[3,4-b]pyridin-3-yl]-1,2,4-triazin-6-yl}-2-methylpropanoate

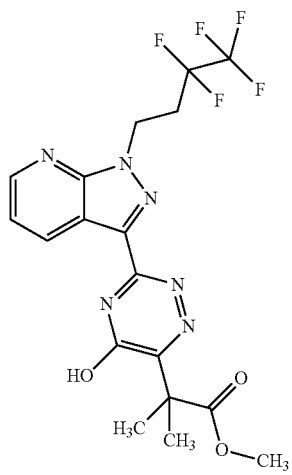 [SMILES: COC(=O)C(C)(C)c1nnc(-c2nn(CCC(F)(F)C(F)(F)F)c3ncccc23)nc1O]

The crude substance from Example 14A (about 1.144 mmol) was dissolved in 15 ml of ethanol, and 430 mg (2.288 mmol) of dimethyl 2,2-dimethyl-3-oxobutanedioate (described in J. Am. Chem. Soc. 124(14), 3680-3691; 2002) were added. The mixture was stirred at RT overnight and then heated at reflux for 1 h. After cooling, the solid was filtered off with suction and washed with ethanol, and the filtrate was concentrated. Diethyl ether was added to the residue, and a precipitate that formed was filtered off and washed with diethyl ether. The filtrate was concentrated and the residue was purified by preparative HPLC (acetonitrile:water (+0.05% formic acid) gradient). This gave 264 mg of the title compound (50% of theory).

LC-MS (Method 2): $R_t$=1.03 min; MS (ESIpos): m/z=461 (M+H)+

$^1$H NMR (400 MHz, DMSO-$d_6$): δ [ppm]=1.46 (s, 6H), 3.06-3.17 (m, 2H), 3.57 (s, 3H), 4.95 (t, 2H), 7.51 (dd, 1H), 8.70 (dd, 1H), 8.75 (dd, 1H), 14.52 (s, 1H).

Example 17A

Methyl 2-{3-[5-fluoro-1-(3,3,4,4,4-pentafluorobutyl)-1H-pyrazolo[3,4-b]pyridin-3-yl]-5-hydroxy-1,2,4-triazin-6-yl}-2-methylpropanoate

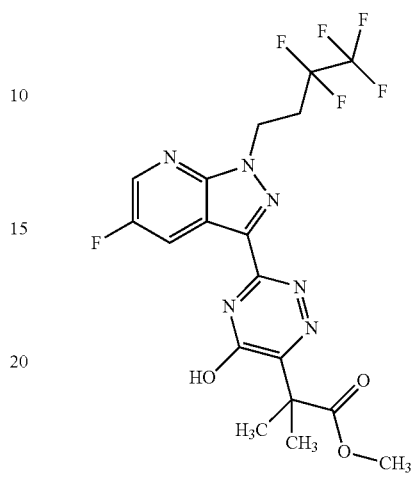

The crude substance from Example 15A (about 0.845 mmol) was dissolved in 10 ml of ethanol, and 318 mg (1.689 mmol) of dimethyl 2,2-dimethyl-3-oxobutanedioate (described in J. Am. Chem. Soc. 124(14), 3680-3691; 2002) were added. The mixture was stirred at RT overnight and then heated at reflux for 6 h. After cooling, the filtrate was concentrated and the residue was purified by preparative HPLC (acetonitrile:water (+0.05% formic acid) gradient). This gave 291 mg of the title compound (72% of theory).

LC-MS (Method 2): $R_t$=1.04 min; MS (ESIpos): m/z=479 (M+H)+

$^1$H NMR (400 MHz, DMSO-$d_6$): δ [ppm]=1.46 (s, 6H), 3.07-3.14 (m, 2H), 3.56 (s, 3H), 4.94 (t, 2H), 8.40 (d, 1H), 8.85 (br s, 1H), 14.56 (s, 1H).

Example 18A

4-Amino-5,5-dimethyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one

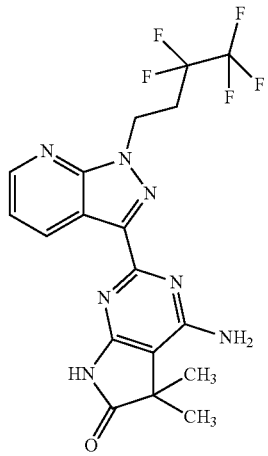 [SMILES: CC1(C)C(=O)Nc2nc(-c3nn(CCC(F)(F)C(F)(F)F)c4ncccc34)nc(N)c21]

500 mg (1.361 mmol) of Example 13A were initially charged in tert-butanol (7.5 ml), and 183 mg (1.361 mmol) of potassium tert-butoxide were added. Subsequently, 226 mg (1.361 mmol) of Example 10A in tert-butanol (2.5 ml) were added dropwise and the mixture was heated to reflux overnight. After cooling, ethyl acetate and water were added, the phases were separated and the aqueous phase was extracted twice with ethyl acetate. The combined organic phases were washed with saturated aqueous sodium chloride solution, dried over sodium sulfate, filtered and concentrated. The residue was stirred with methanol and a solid was filtered off with suction. This solid was washed vigorously with methanol, and the combined filtrates were concentrated and then purified by means of preparative HPLC (acetonitrile:water (+0.05% formic acid) gradient). This gave 127 mg of the title compound (21% of theory).

LC-MS (Method 2): $R_t$=0.93 min; MS (ESIpos): m/z=442 (M+H)+

$^1$H NMR (400 MHz, DMSO-$d_6$): δ [ppm]=1.36 (s, 6H), 2.91-3.04 (m, 2H), 4.88 (t, 2H), 6.83 (br s, 2H), 7.38 (dd, 1H), 8.63 (dd, 1H), 9.02 (dd, 1H), 11.01 (br s, 1H).

Example 19A

4-Amino-2-[5-fluoro-1-(3,3,4,4,4-pentafluorobutyl)-1H-pyrazolo[3,4-b]pyridin-3-yl]-5,5-dimethyl-5,7-dihydro-6H-pyrrolo[2,3-d]pyrimidin-6-one

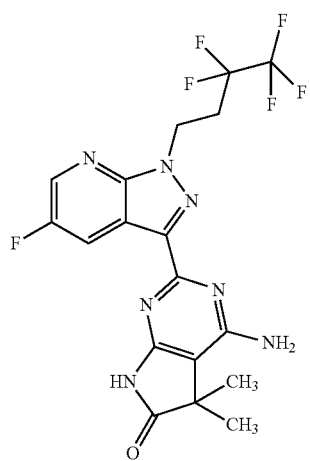 [SMILES: CC1(C)C(=O)Nc2nc(-c3nn(CCC(F)(F)C(F)(F)F)c4ncc(F)cc34)nc(N)c21]

520 mg (1.350 mmol) of Example 9A were initially charged in tert-butanol (10 ml), and 181 mg (1.620 mmol) of potassium tert-butoxide were added. Subsequently, 224 mg (1.350 mmol) of Example 10A in tert-butanol (2.5 ml) were added and the mixture was heated to reflux overnight. Another 112 mg (0.675 mmol) of Example 10A were then added, and the mixture was heated at reflux for a further 7.5 h. After cooling, water and ethanol were added and the reaction mixture was treated in an ultrasonic bath for 1 h. The precipitate formed was filtered off with suction and washed with water. The filter cake was stirred with a little ethanol (2-3 ml) and once more filtered off with suction. The solid was dried under high vacuum. This gave 212 mg of the title compound (34% of theory).

LC-MS (Method 1): $R_t$=1.01 min; MS (ESIpos): m/z=460 (M+H)$^+$ $^1$H NMR (400 MHz, DMSO-$d_6$): δ [ppm]=1.36 (s, 6H), 2.92-3.04 (m, 2H), 4.87 (t, 2H), 6.88 (br s, 2H), 8.71 (br s, 1H), 8.85 (dd, 1H), 11.01 (br s, 1H).

Example 20A

4-Iodo-5,5-dimethyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one

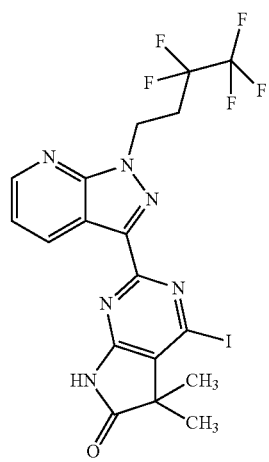 [SMILES: CC1(C)C(=O)Nc2nc(-c3nn(CCC(F)(F)C(F)(F)F)c4ncccc34)nc(I)c21]

155 mg (0.351 mmol) of Example 18A were initially charged in isopentyl nitrite (1.017 ml) and diiodomethane (2.655 ml) and heated at 85° C. for 2 d. After cooling, a solid was filtered off and washed with cyclohexane, and the solid was then purified by preparative HPLC (acetonitrile:water (+0.05% formic acid) gradient). This gave 39 mg of the title compound (20% of theory).

LC-MS (Method 2): $R_t$=1.21 min; MS (ESIpos): m/z=553 (M+H)$^+$ $^1$H NMR (400 MHz, DMSO-$d_6$): δ [ppm]=1.44 (s, 6H), 2.96-3.06 (m, 2H), 4.94 (t, 2H), 7.48 (dd, 1H), 8.69 (dd, 1H), 8.79 (dd, 1H), 11.80 (br s, 1H).

Example 21A

2-[5-Fluoro-1-(3,3,4,4,4-pentafluorobutyl)-1H-pyrazolo[3,4-b]pyridin-3-yl]-4-iodo-5,5-dimethyl-5,7-dihydro-6H-pyrrolo[2,3-d]pyrimidin-6-one

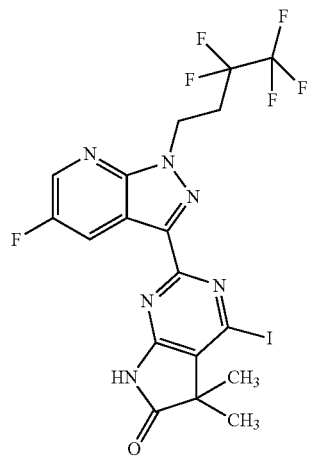 [SMILES: CC1(C)C(=O)Nc2nc(-c3nn(CCC(F)(F)C(F)(F)F)c4ncc(F)cc34)nc(I)c21]

142 mg (0.310 mmol) of Example 19A were initially charged in isopentyl nitrite (0.90 ml) and diiodomethane (2.4 ml) and heated at 85° C. overnight. More isopentyl nitrite (1 ml) was then added, and the mixture was heated at 85° C. for a further 22 h. More isopentyl nitrite (1 ml) was then added, and the mixture was heated at 85° C. for a further 12 h. After cooling, the mixture was purified by preparative HPLC (acetonitrile:water (+0.05% formic acid) gradient). This gave 71 mg of the title compound (40% of theory).

LC-MS (Method 2): $R_t$=1.28 min; MS (ESIpos): m/z=571 (M+H)$^+$

Example 22A 1-(Cyclopentylmethyl)-5-fluoro-3-iodo-1H-pyrazolo[3,4-b]pyridine

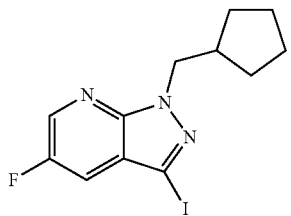 [SMILES: Fc1cnc2c(c1)c(I)nn2CC1CCCC1]

10.000 g (38.021 mmol) of 5-fluoro-3-iodo-1H-pyrazolo[3,4-b]pyridine and 13.627 g (41.823 mmol) of cesium carbonate were initially charged in 270 ml of DMF, and 8.785 g (41.823 mmol) of (iodomethyl)cyclopentane were added. The reaction mixture was stirred at RT overnight, diluted with water and extracted with ethyl acetate. The organic phase was dried over sodium sulfate and concentrated on a rotary evaporator. This gave 6.370 g of the target compound (purity 83%, 49% of theory), which was reacted further as a crude product.

LC-MS (Method 2): $R_t$=1.37 min; MS (ESIpos): m/z=346 (M+H)$^+$

Example 23A 1-(Cyclopentylmethyl)-5-fluoro-1H-pyrazolo[3,4-b]pyridine-3-carbonitrile

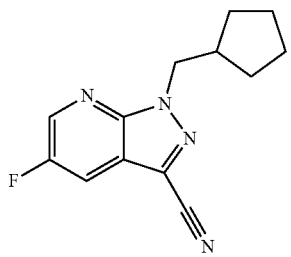 [SMILES: N#Cc1nn(CC2CCCC2)c2ncc(F)cc12]

Under an atmosphere of argon, 6.370 g (purity 83%, 15.447 mmol) of 1-(cyclopentylmethyl)-5-fluoro-3-iodo-1H-pyrazolo[3,4-b]pyridine and 1.522 g (16.992 mmol) of copper(I) cyanide were initially charged in 45 ml of absolute DMSO, and the mixture was heated at 150° C. for 1.5 h. After cooling, the reaction was diluted with methanol and filtered through Celite. The organic phase was washed twice with a mixture of 25% strength aqueous ammonia solution and saturated aqueous ammonium chloride solution (v/v=1:3), then washed with a saturated aqueous sodium chloride solution, dried over sodium sulfate and concentrated on a rotary evaporator. This gave 3.670 g (purity 86%, 97% of theory) of the target compound.

LC-MS (Method 1): $R_t$=2.56 min; MS (ESIpos): m/z=245 (M+H)$^+$

Example 24A 1-(Cyclopentylmethyl)-5-fluoro-1H-pyrazolo[3,4-b]pyridine-3-carboximidamide acetate

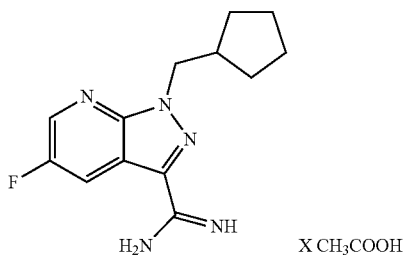

Under an atmosphere of argon, 296 mg (12.861 mmol) of sodium were, a little at a time, stirred into methanol. After the sodium had been consumed, 3.670 g (purity 86%, about 12.861 mmol) of 1-(cyclopentylmethyl)-5-fluoro-1H-pyrazolo[3,4-b]pyridine-3-carbonitrile were added a little at a time, and the mixture was stirred at RT for 2 h. 3.004 g (50.021 mmol) of acetic acid and 825 mg (15.433 mmol) of ammonium chloride were then added, and the mixture was boiled under reflux overnight. The reaction mixture was concentrated, the residue was triturated with 1N sodium hydroxide solution and the precipitate was filtered off with suction and dried under high vacuum. This gave 2.840 g (purity 98%, 83% of theory) of the target compound.

LC-MS (Method 2): $R_t$=0.67 min; MS (ESIpos): m/z=262 (M+H)$^+$

Example 25A

4-Amino-2-[1-(cyclopentyl methyl)-5-fluoro-1H-pyrazolo[3,4-b]pyridin-3-yl]-5,5-dimethyl-5,7-dihydro-6H-pyrrolo[2,3-d]pyrimidin-6-one

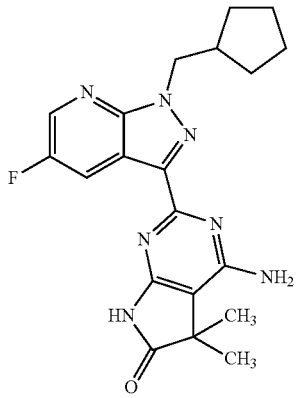 [SMILES: CC1(C)C(=O)Nc2nc(-c3nn(CC4CCCC4)c4ncc(F)cc34)nc(N)c21]

30 ml of tert-butanol, 1.068 g (6.429 mmol) of methyl 3,3-dicyano-2,2-dimethylpropanoate dissolved in 15 ml of tert-butanol and 901 mg (8.037 mmol) of potassium tert-butoxide were added to 1.400 g (5.358 mmol) of 1-(cyclopentylmethyl)-5-fluoro-1H-pyrazolo[3,4-b]pyridine-3-carboximidamide, and the mixture was heated under reflux for 24 h. The reaction mixture was concentrated on a rotary evaporator, triturated with 60 ml of water/ethanol (v/v=5:1), filtered off with suction and dried under high vacuum. This gave 1.296 g (57% of theory) of the target compound.

LC-MS (Method 1) R$_t$=1.04 min; MS (ESIpos): m/z=396 (M+H)$^+$

Example 26A

2-[1-(Cyclopentylmethyl)-5-fluoro-1H-pyrazolo[3,4-b]pyridin-3-yl]-4-iodo-5,5-dimethyl-5,7-dihydro-6H-pyrrolo[2,3-d]pyrimidin-6-one

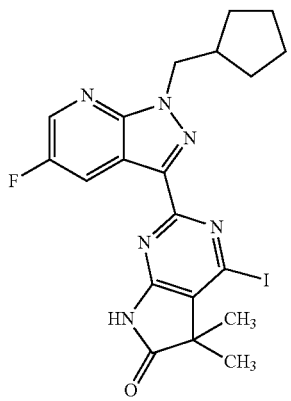 [SMILES: CC1(C)C(=O)Nc2nc(-c3nn(CC4CCCC4)c4ncc(F)cc34)nc(I)c21]

40.549 g (151.398 mmol) of diiodomethane and 4.420 g (37.738 mmol) of isopentyl nitrite were added to 711 mg (1.799 mmol) of 4-amino-2-[1-(cyclopentylmethyl)-5-fluoro-1H-pyrazolo[3,4-b]pyridin-3-yl]-5,5-dimethyl-5,7-dihydro-6H-pyrrolo[2,3-d]pyrimidin-6-one. The mixture was stirred at 85° C. for 8 h. After cooling, the mixture was filtered, and the filtrate was diluted with cyclohexane and sucked through silica gel. The silica gel was washed with cyclohexane and the product was eluted with dichloromethane/methanol (v/v=50:2). The collected fractions were concentrated on a rotary evaporator, taken up in 20 ml of ethyl acetate and 5 ml of isopropanol, filtered and concentrated again. The residue was triturated with 5 ml of isopropanol. The solid was filtered off with suction and dried under high vacuum. This gave 230 mg (purity 92%, 23% of theory) of the target compound.

LC-MS (Method 1) R$_t$=1.41 min; MS (ESIpos): m/z=507 (M+H)$^+$

Example 27A 1-(Cyclopentylmethyl)-5-fluoro-1H-pyrazolo[3,4-b]pyridine-3-carboximidohydrazide

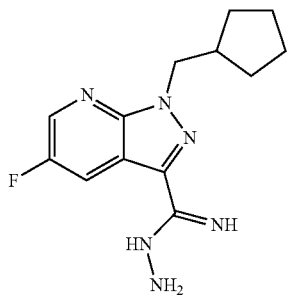 [SMILES: N=C(NN)c1nn(CC2CCCC2)c2ncc(F)cc12]

1.400 g (5.358 mmol) of 1-(cyclopentylmethyl)-5-fluoro-1H-pyrazolo[3,4-b]pyridine-3-carboximidamide were initially charged in 26 ml of ethanol, and the mixture was cooled to 0° C. 2.169 g (21.431 mmol) of triethylamine and 335 mg (5.358 mmol) of 80% strength hydrazine hydrate were added, and the mixture was stirred at room temperature for 18 h. The mixture was concentrated on a rotary evaporator, taken up in ethyl acetate and washed three times with saturated aqueous sodium chloride solution. The organic phase was dried over sodium sulfate, concentrated on a rotary evaporator and dried under high vacuum. This gave 1.070 g (purity 77%, 56% of theory) of the target compound.

LC-MS (Method 2): R$_t$=0.67 min; MS (ESIpos): m/z=277 (M+H)$^+$

Example 28A

Methyl 2-{3-[1-(cyclopentylmethyl)-5-fluoro-1H-pyrazolo[3,4-b]pyridin-3-yl]-5-hydroxy-1,2,4-triazin-6-yl}-2-methylpropanoate

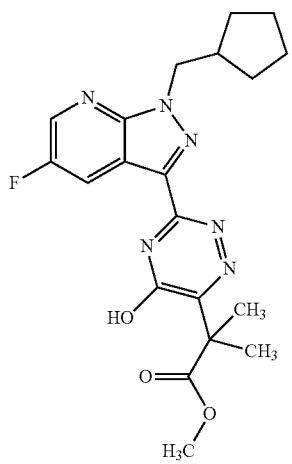 [SMILES: COC(=O)C(C)(C)c1nnc(-c2nn(CC3CCCC3)c3ncc(F)cc23)nc1O]

841 mg (4.473 mmol) of dimethyl 2,2-dimethyl-3-oxobutanedioate were initially charged in 20 ml of ethanol, and the mixture was heated to reflux. Subsequently, 1.070 g (2.982 mmol) of 1-(cyclopentylmethyl)-5-fluoro-1H-pyrazolo[3,4-b]pyridine-3-carboximidohydrazide suspended in 26 ml of ethanol were added, and the mixture was boiled under reflux overnight. After cooling, the mixture was concentrated, taken up in acetonitrile and filtered. The filtrate was purified by preparative HPLC (mobile phase: acetonitrile/water, gradient 30:70→100:0). This gave 396 mg of the target compound (32% of theory).

LC-MS (Method 2): R$_t$=1.15 min; MS (ESIpos): m/z=415 (M+H)$^+$

Example 29A

5-Fluoro-3-iodo-1-(4-methoxybenzyl)-1H-pyrazolo[3,4-b]pyridine

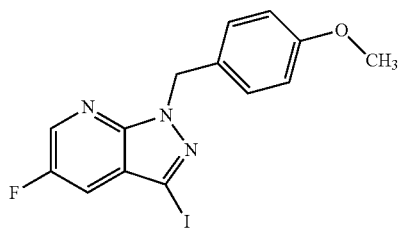 [SMILES: COc1ccc(Cn2nc(I)c3cc(F)cnc32)cc1]

10.00 g (38.021 mmol) of Example 6A were reacted analogously to the procedure of Example 22A with 4-methoxybenzyl chloride. Chromatography on silica gel (mobile phase: cyclohexane/ethyl acetate mixture) gave 8.94 g (61% of theory) of the title compound.

LC-MS (Method 1): $R_t$=1.25 min

MS (ESIpos): m/z=384 (M+H)$^+$

Example 30A

5-Fluoro-1-(4-methoxybenzyl)-1H-pyrazolo[3,4-b]pyridine-3-carbonitrile

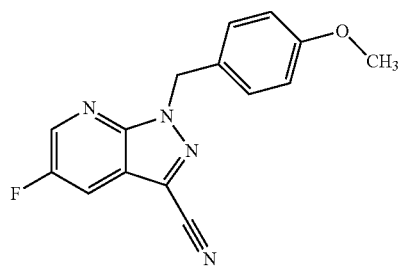 [SMILES: COc1ccc(Cn2nc(C#N)c3cc(F)cnc32)cc1]

8.94 g (23.332 mmol) of Example 29A were reacted analogously to the procedure of Example 23A. The crude product obtained in this manner was reacted without further purification.

Yield: 6.52 g (99% of theory)

LC-MS (Method 2): $R_t$=1.11 min

MS (ESIpos): m/z=283 (M+H)$^+$

Example 31A

5-Fluoro-1-(4-methoxybenzyl)-1H-pyrazolo[3,4-b]pyridine-3-carboximidamide acetate

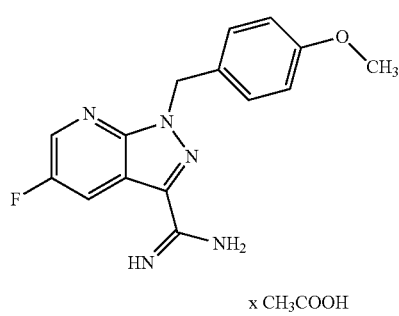 [SMILES: COc1ccc(Cn2nc(C(=N)N)c3cc(F)cnc32)cc1 ; "x CH3COOH"]

6.52 g (23.098 mmol) of Example 30A were reacted analogously to the procedure of Example 13A. Yield: 6.16 g (74% of theory)

LC-MS (Method 1): $R_t$=0.55 min

MS (ESIpos): m/z=300 (M+H)$^+$

Example 32A

5-Fluoro-1-(4-methoxybenzyl)-1H-pyrazolo[3,4-b]pyridine-3-carboximidohydrazide

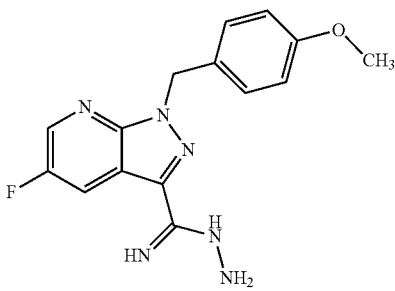 [SMILES: COc1ccc(Cn2nc(C(=N)NN)c3cc(F)cnc32)cc1]

6.16 g (17.141 mmol) of Example 31A were reacted analogously to the procedure of Example 27A. This gave 4.90 g (90% of theory) of the title compound.

LC-MS (Method 1): $R_t$=0.57 min; MS (ESIpos): m/z=315 (M+H)$^+$

Example 33A

Methyl 2-{3-[5-fluoro-1-(4-methoxybenzyl)-1H-pyrazolo[3,4-b]pyridin-3-yl]-5-hydroxy-1,2,4-triazin-6-yl}-2-methylpropanoate

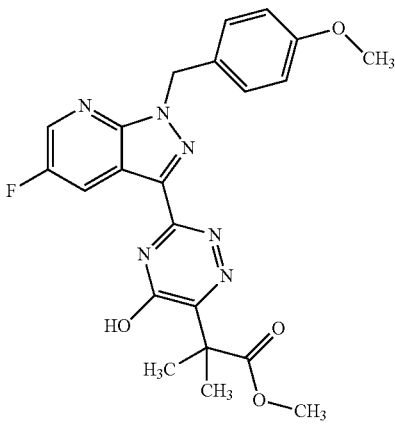 [SMILES: COC(=O)C(C)(C)c1nnc(-c2nn(Cc3ccc(OC)cc3)c3ncc(F)cc23)nc1O]

4.89 g (15.557 mmol) of the compound from Example 32A were reacted analogously to the procedure of Example 28A with 4.391 g (23.336 mmol) of dimethyl 2,2-dimethyl-3-oxobutanedioate (described in J. Am. Chem. Soc. 124(14), 3680-3691; 2002). After the reaction had gone to completion, a solid was filtered off, which was washed with ethanol and then dried under high vacuum. This gave 6.04 g (85% of theory) of the title compound.

LC-MS (Method 1): $R_t$=1.05 min; MS (ESIpos): m/z=453 (M+H)$^+$

Example 34A

3-[5-Fluoro-1-(4-methoxybenzyl)-1H-pyrazolo[3,4-b]pyridin-3-yl]-7,7-dimethyl-5,7-dihydro-6H-pyrrolo[2,3-e][1,2,4]triazin-6-one

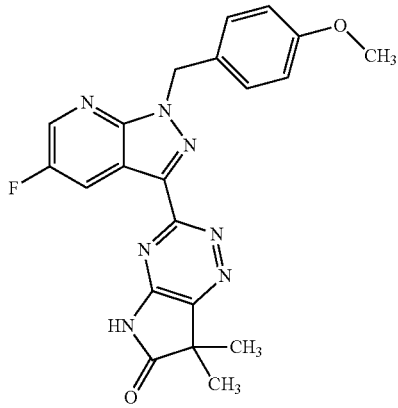 [SMILES: COc1ccc(Cn2nc(-c3nnc4c(n3)NC(=O)C4(C)C)c3cc(F)cnc32)cc1]

6.04 g (13.350 mmol) of the compound from Example 33A were reacted analogously to the procedure of Example 1. This gave, after drying under high vacuum, 1.27 g (22% of theory) of the title compound.

LC-MS (Method 2): $R_t$=1.02 min; MS (EIpos): m/z=420 [M+H]$^+$.

$^1$H NMR (400 MHz, DMSO-d$_6$): δ [ppm]=1.45 (s, 6H), 3.70 (s, 3H), 5.75 (s, 2H), 6.88 (d, 2H), 7.29 (d, 2H), 8.53 (dd, 1H), 8.78 (dd, 1H), 12.18 (s br, 1H).

Example 35A

3-[5-Fluoro-1-(4-methoxybenzyl)-1H-pyrazolo[3,4-b]pyridin-3-yl]-7,7-dimethyl-5-{[2-(trimethylsilyl)ethoxy]methyl}-5,7-dihydro-6H-pyrrolo[2,3-e][1,2,4]triazin-6-one

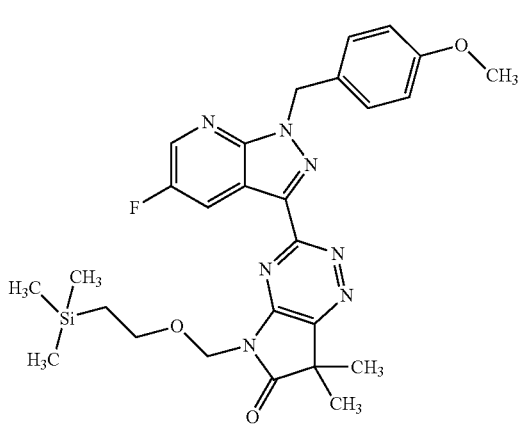

2.067 g (6.345 mmol) of cesium carbonate in DMF (30 ml) were added to 2.45 g (5.768 mmol) of the compound from Example 34A. 1.221 ml (6.922 mmol) of 2-(trimethylsilyl)ethoxymethyl chloride were then added, and the mixture was stirred at room temperature for 1 h. The solids were then filtered off and washed with DMF, the filtrate was concentrated and the residue was dried under high vacuum. This gave 4.45 g of crude material which were used without further purification for the next step.

LC-MS (Method 2): $R_t$=1.43 min; MS (EIpos): m/z=550 [M+H]$^+$.

Example 36A 3-(5-Fluoro-1H-pyrazolo[3,4-b]pyridin-3-yl)-7,7-dimethyl-5-{[2-(trimethylsilyl)ethoxy]methyl}-5,7-dihydro-6H-pyrrolo[2,3-e][1,2,4]triazin-6-one

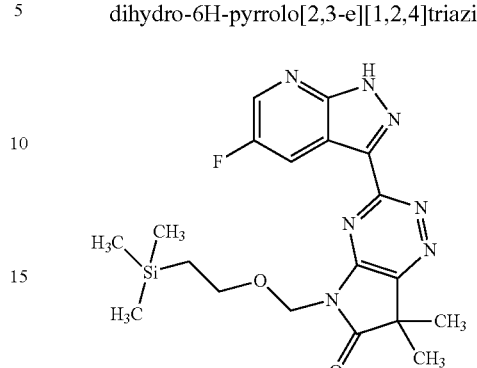

4.148 g (7.546 mmol) of the compound from Example 35A were taken up in acetonitrile (110 ml) and water (55 ml), 12.411 g (22.638 mmol) of ammonium cerium(IV) nitrate were added and the mixture was stirred at room temperature for 20 min. Plenty of water was then added, and a precipitate was filtered off. This solid was washed with water and then with a little diethyl ether. This gave, after drying under high vacuum, 1.53 g (47% of theory) of the title compound.

LC-MS (Method 2): $R_t$=1.14 min; MS (EIpos): m/z=430 [M+H]$^+$.

Example 37A

3-[5-Fluoro-1-(3,3,4,4-tetrafluorobutyl)-1H-pyrazolo[3,4-b]pyridin-3-yl]-7,7-dimethyl-5-{[2-(trimethylsilyl)ethoxy]methyl}-5,7-dihydro-6H-pyrrolo[2,3-e][1,2,4]triazin-6-one

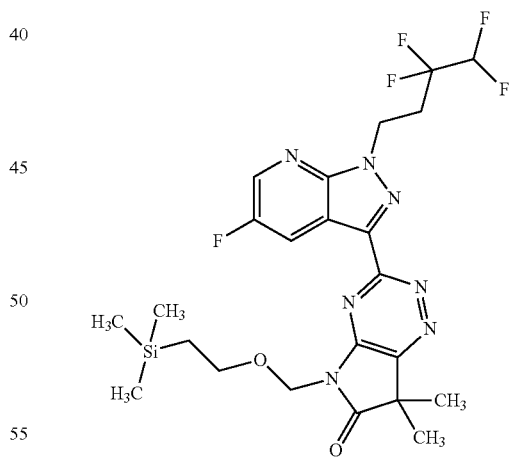

0.150 g (0.349 mmol) of the compound from Example 36A were reacted analogously to the procedure of Example 7A with 1-bromo-3,3,4,4-tetrafluorobutane. In this case, no potassium iodide was added. After filtration, the product was purified by preparative HPLC (acetonitrile:water (+0.05% formic acid) gradient). This gave 97 mg of the title compound as a mixture of isomers (N1/N2-alkylated, ratio 3.2:1) (50% of theory).

LC-MS (Method 2): $R_t$=1.36 min (N2) and 1.38 min (N1); MS (EIpos): m/z=558 [M+H]$^+$.

Example 38A

3-{1-[(3,3-Difluorocyclobutyl)methyl]-5-fluoro-1H-pyrazolo[3,4-b]pyridin-3-yl}-7,7-dimethyl-5-{[2-(trimethylsilyl)ethoxy]methyl}-5,7-dihydro-6H-pyrrolo[2,3-e][1,2,4]triazin-6-one

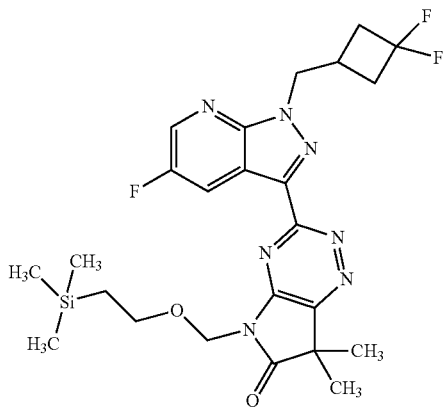 [SMILES: CC1(C)C(=O)N(COCC[Si](C)(C)C)c2nc(-c3nn(CC4CC(F)(F)C4)c4ncc(F)cc34)nnc21]

In a flask, 137 mg (0.524 mmol) of triphenylphosphine were dissolved in 4 ml of tetrahydrofuran, and the mixture was cooled to 0° C. 101 µl (0.524 mmol) of diisopropyl azodicarboxylate were then added, and the solution was stirred at 0° C. for 1 h (solution 1). In a further flask, 0.150 g (0.349 mmol) of the compound from Example 36A and 64 mg (0.542 mmol) of 3,3-difluorocyclobutylmethanol were dissolved in tetrahydrofuran (6 ml), and the mixture was cooled to 0° C. (solution 2). Solution 1 was then added to this solution 2, and the mixture was stirred at room temperature overnight. Subsequently, solution 1 was once more prepared as described above using 274 mg (1.048 mmol) of triphenylphosphine and 203 µl (1.048 mmol) of diisopropyl azodicarboxylate and, together with 127 mg (1.048 mmol) of 3,3-difluorocyclobutylmethanol and dichloromethane (5 ml), added to the reaction at 0° C. After stirring overnight at room temperature, the product was purified by preparative HPLC (acetonitrile:water (+0.05% formic acid) gradient). This gave 102 mg of the title compound as a mixture of isomers (N1/N2-alkylated, ratio 1.4:1) (55% of theory).

LC-MS (Method 2): $R_t$=1.38 min (N2) and 1.41 min (N1); MS (EIpos): m/z=558 [M+H]$^+$.

Example 39A

Diethyl (dicyanomethyl)(methyl)malonate

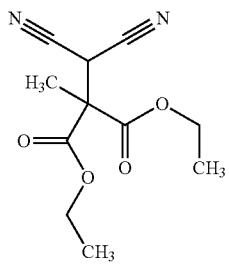 [SMILES: CCOC(=O)C(C)(C(=O)OCC)C(C#N)C#N]

19.156 g (75.686 mmol) of diethyl 2-bromo-2-methylmalonate were initially charged in THF (120 ml), and 5 g (75.686 mmol) of malononitrile and then 8.493 g (75.686 mmol) of potassium tert-butoxide were added. The mixture was then heated to reflux overnight. Ethyl acetate and sat. ammonium chloride solution were then added to the reaction, and the phases were separated. The aqueous phase was extracted two more times with ethyl acetate. The combined organic phases were washed with saturated aqueous sodium chloride solution, dried over sodium sulfate, filtered and concentrated to dryness. This gave a crude product which was purified by chromatography on silica gel (cyclohexane/ethyl acetate 9:1).

Yield: 5.94 g (32% of theory)
$^1$H NMR (400 MHz, CDCl$_3$): δ [ppm]=1.32 (t, 6H), 1.80 (s, 3H), 4.28-4.37 (m, 4H), 4.53 (s, 1H).

Example 40A

Ethyl 4-amino-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxylate

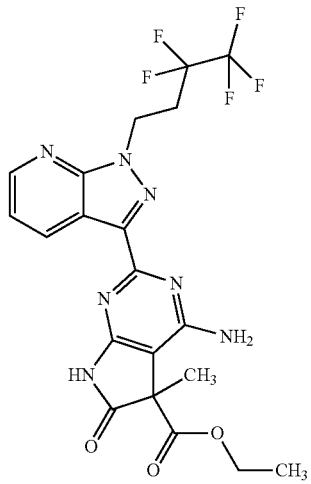 [SMILES: CCOC(=O)C1(C)C(=O)Nc2nc(-c3nn(CCC(F)(F)C(F)(F)F)c4ncccc34)nc(N)c21]

0.5 g (1.361 mmol) of Example 13A (purity 70%) was initially charged in tert-butanol (10 ml), and 272 mg (2.723 mmol) of potassium bicarbonate were added. 372 mg (1.566 mmol) of Example 39A were then added, and the mixture was heated at reflux for 5 h. After cooling, water was added, the mixture was stirred for 30 min and a precipitate was then filtered off. The precipitate was washed with a little water and diethyl ether and dried under high vacuum overnight. This gave 0.458 g (63% of theory) of the title compound in a purity of 94%.

LC-MS (Method 2): $R_t$=1.00 min; MS (ESIpos): m/z=500 (M+H)$^+$

Example 41A

Ethyl 4-bromo-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxylate

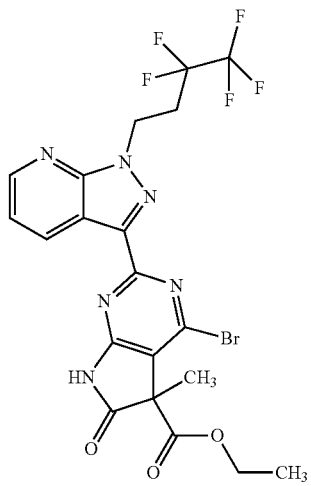 [SMILES: CCOC(=O)C1(C)C(=O)Nc2nc(-c3nn(CCC(F)(F)C(F)(F)F)c4ncccc34)nc(Br)c21]

437 mg (0.875 mmol) of Example 40A were initially charged in 1,2-dichloroethane (14.2 ml), and 0.176 ml (1.313 mmol) of isopentyl nitrite and 234 mg (1.050 mmol) of copper(II) bromide were added. The mixture was then heated at 65° C. for 10 h. After cooling, water and dichloromethane were added and the phases were separated. The aqueous phase was once added with ethyl acetate, and the combined organic phases were dried over sodium sulfate and concentrated, and the residue was purified by preparative chromatography on silica gel (mobile phase: dichloromethane/methanol 66:1). This gave 0.393 g (89% of theory) of the title compound in a purity of about 90%.

LC-MS (Method 2): $R_t$=1.23 min; MS (ESIpos): m/z=563 ($^{79}$Br), 565 ($^{81}$Br) (M+H)$^+$

WORKING EXAMPLES

Example 1

7,7-Dimethyl-3-[1-(3,3,4,4,4-pentafluorobutyl)-1H-pyrazolo[3,4-b]pyridin-3-yl]-5,7-dihydro-6H-pyrrolo[2,3-e][1,2,4]triazin-6-one

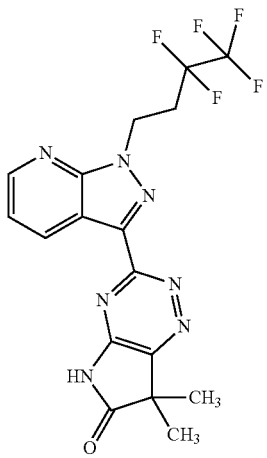 [SMILES: CC1(C)C(=O)Nc2nc(-c3nn(CCC(F)(F)C(F)(F)F)c4ncccc34)nnc21]

4 ml of phosphoryl chloride were added to 263 mg (0.571 mmol) of the compound from Example 16A, and the mixture was stirred at RT overnight. The reaction mixture was dissolved in 38 ml of acetonitrile and, with ice-cooling, stirred into 24 ml of concentrated aqueous ammonia solution (33% strength). The mixture was stirred at RT for 2 days. The reaction mixture was then concentrated. The residue was taken up in water and ethanol and stirred at RT for 1 h. The precipitate formed was filtered off with suction and washed with water and ethanol. This residue was purified by preparative HPLC (acetonitrile:water (+0.05% formic acid) gradient). This gave 119 mg of the title compound (49% of theory).

LC-MS (Method 2): $R_t$=0.98 min; MS (EIpos): m/z=428 [M+H]$^+$.

$^1$H NMR (400 MHz, DMSO-d$_6$): δ [ppm]=1.47 (s, 6H), 2.96-3.07 (m, 2H), 4.95 (t, 2H), 7.48 (dd, 1H), 8.71 (dd, 1H), 8.85 (dd, 1H), 12.21 (br s, 1H).

Example 2

3-[5-Fluoro-1-(3,3,4,4,4-pentafluorobutyl)-1H-pyrazolo[3,4-b]pyridin-3-yl]-7,7-dimethyl-5,7-dihydro-6H-pyrrolo[2,3-e][1,2,4]triazin-6-one

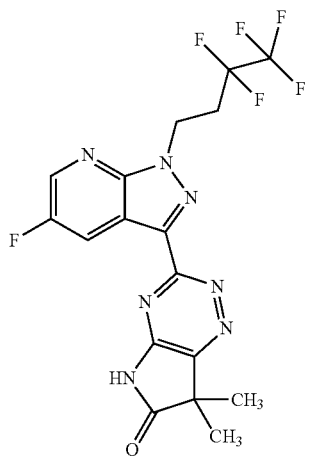 [SMILES: CC1(C)C(=O)Nc2nc(-c3nn(CCC(F)(F)C(F)(F)F)c4ncc(F)cc34)nnc21]

4.172 ml of phosphoryl chloride were added to 290 mg (0.606 mmol) of the compound from Example 17A, and the mixture was stirred at RT overnight. The reaction mixture was dissolved in 40 ml of acetonitrile and, with ice-cooling, stirred into 27 ml of concentrated aqueous ammonia solution (33% strength). The mixture was stirred at room temperature for 2 days. The mixture was then concentrated. The residue was taken up in water and ethanol and treated in an ultrasonic bath. A precipitate was formed, which was filtered off with suction and washed with water, ethanol and then with diethyl ether. DMF was added to this residue, acetonitrile and water were added and the mixture was then once more filtered off with suction. The precipitate was washed with acetonitrile and water and then dried under high vacuum. This gave 149 mg of the title compound (52% of theory, purity 94%).

LC-MS (Method 2): $R_t$=1.05 min; MS (EIpos): m/z=446 [M+H]$^+$ $^1$H NMR (400 MHz, DMSO-d$_6$): δ [ppm]=1.47 (s, 6H), 2.96-3.07 (m, 2H), 4.95 (t, 2H), 8.56 (dd, 1H), 8.80 (br s, 1H), 12.21 (br s, 1H).

Example 3

5,5-Dimethyl-2-[1-(3,3,4,4,4-pentafluorobutyl)-1H-pyrazolo[3,4-b]pyridin-3-yl]-5,7-dihydro-6H-pyrrolo[2,3-d]pyrimidin-6-one

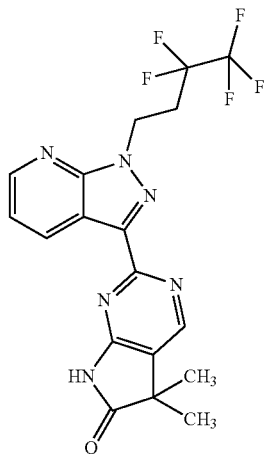 [SMILES: CC1(C)C(=O)Nc2nc(-c3nn(CCC(F)(F)C(F)(F)F)c4ncccc34)ncc21]

39 mg (0.071 mmol) of Example 20A were dissolved in DMF (4 ml) and added to 20 mg of palladium on carbon (10%) in 1 ml DMF, and the mixture was hydrogenated at standard pressure for 12 h. The mixture was then filtered through Celite, the filter cake was washed with DMF and the filtrate was concentrated to dryness. The residue was purified by means of preparative HPLC (acetonitrile:water (+0.05% formic acid) gradient). This gave 22 mg of the title compound (74% of theory).

LC-MS (Method 2): $R_t$=1.02 min; MS (ESIpos): m/z=427 (M+H)+

$^1$H NMR (400 MHz, DMSO-$d_6$): δ [ppm]=1.39 (s, 6H), 2.96-3.06 (m, 2H), 4.92 (t, 2H), 7.43 (dd, 1H), 8.66-8.69 (m, 2H), 8.86 (dd, 1H), 11.61 (br s, 1H).

Example 4

2-[5-Fluoro-1-(3,3,4,4,4-pentafluorobutyl)-1H-pyrazolo[3,4-b]pyridin-3-yl]-5,5-dimethyl-5,7-dihydro-6H-pyrrolo[2,3-d]pyrimidin-6-one

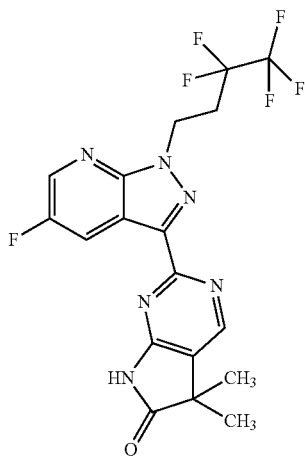 [SMILES: CC1(C)C(=O)Nc2nc(-c3nn(CCC(F)(F)C(F)(F)F)c4ncc(F)cc34)ncc21]

39 mg (0.068 mmol) of Example 21A were dissolved in DMF (5 ml), 20 mg of palladium on carbon (10%) were added and the mixture was hydrogenated at standard pressure for 12 h. The mixture was then filtered through Celite, the filter cake was washed with DMF and the filtrate was concentrated to dryness. The residue was purified by means of preparative HPLC (acetonitrile:water (+0.05% formic acid) gradient). This gave 8 mg of the title compound (74% of theory).

LC-MS (Method 2): $R_t$=1.10 min; MS (ESIpos): m/z=445 (M+H)$^+$ $^1$H NMR (400 MHz, DMSO-$d_6$): δ [ppm]=1.39 (s, 6H), 2.96-3.06 (m, 2H), 4.91 (t, 2H), 8.59 (dd, 1H), 8.65 (m, 1H), 8.76 (dd, 1H), 11.60 (br s, 1H).

Example 5

2-[1-(Cyclopentylmethyl)-5-fluoro-1H-pyrazolo[3,4-b]pyridin-3-yl]-5,5-dimethyl-5,7-dihydro-6H-pyrrolo[2,3-d]pyrimidin-6-one

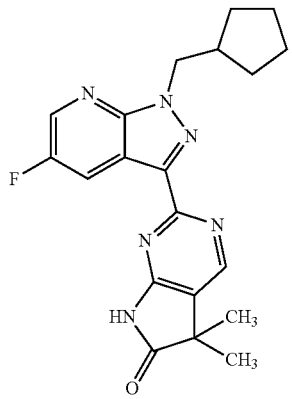 [SMILES: CC1(C)C(=O)Nc2nc(-c3nn(CC4CCCC4)c4ncc(F)cc34)ncc21]

230 mg (0.454 mmol) of 2-[1-(cyclopentylmethyl)-5-fluoro-1H-pyrazolo[3,4-b]pyridin-3-yl]-4-iodo-5,5-dimethyl-5,7-dihydro-6H-pyrrolo[2,3-d]pyrimidin-6-one were dissolved in 8 ml of absolute DMF, 150 mg of 10% palladium on carbon were added and the mixture was hydrogenated with hydrogen at standard pressure for 3 h. The reaction mixture was filtered through Celite and concentrated. The residue was triturated with 4 ml of acetonitrile, filtered off with suction and dried under high vacuum. This gave 123 mg of the target compound (purity 94%, 67% of theory).

LC-MS (Method 1) $R_t$=1.18 min; MS (ESIpos): m/z=381 (M+H)$^+$ $^1$H NMR (400 MHz, DMSO-$d_6$): δ [ppm]=1.30-1.65 (m, 14H), 2.56-2.63 (m, 1H), 4.50 (d, 2H), 8.57 (dd, 1H), 8.65 (s, 1H), 8.71 (dd, 1H), 11.64 (s br, 1H).

Example 6

3-[1-(Cyclopentylmethyl)-5-fluoro-1H-pyrazolo[3,4-b]pyridin-3-yl]-7,7-dimethyl-5,7-dihydro-6H-pyrrolo[2,3-e][1,2,4]triazin-6-one

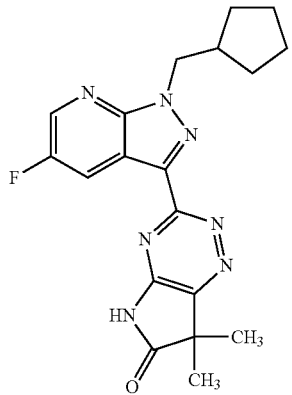 [SMILES: CC1(C)C(=O)Nc2nc(-c3nn(CC4CCCC4)c4ncc(F)cc34)nnc21]

5 ml (53.642 mmol) of phosphoryl chloride were added to 376 mg (0.863 mmol) of methyl 2-{3-[1-(cyclopentylmethyl)-5-fluoro-1H-pyrazolo[3,4-b]pyridin-3-yl]-5-hydroxy-1,2,4-triazin-6-yl}-2-methylpropanoate, and the mixture was stirred at RT overnight. The reaction solution was diluted with 20 ml of dry acetonitrile and, with ice-cooling, slowly added dropwise to 83 ml of a 25% strength aqueous ammonia solution, and the mixture was stirred at RT overnight. The reaction mixture was concentrated on a rotary evaporator and the precipitate was filtered off. The residue was triturated with DMF/methanol, filtered off with suction and dried under high vacuum. This gave 84 mg of the target compound (24% of theory).

LC-MS (Method 1) $R_t$=1.12 min; MS (ESIpos): m/z=382 $(M+H)^+$ $^1$H NMR (400 MHz, DMSO-$d_6$): δ [ppm]=1.30-1.65 (m, 14H), 2.57-2.63 (m, 1H), 4.53 (d, 2H), 8.54 (dd, 1H), 8.74 (dd, 1H).

Example 7

3-[5-Fluoro-1-(3,3,4,4-tetrafluorobutyl)-1H-pyrazolo[3,4-b]pyridin-3-yl]-7,7-dimethyl-5,7-dihydro-6H-pyrrolo[2,3-e][1,2,4]triazin-6-one

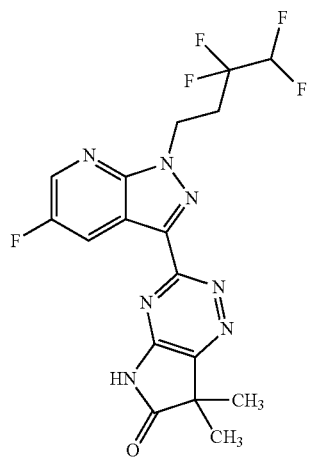 [SMILES: CC1(C)C(=O)Nc2nc(-c3nn(CCC(F)(F)C(F)F)c4ncc(F)cc34)nnc21]

96 mg (0.173 mmol) of the compound from Example 37A were stirred in dichloromethane (4 ml) and trifluoroacetic acid (1 ml) at room temperature for 4.5 h. The mixture was then concentrated to dryness. The residue was stirred in ethanol/2N hydrochloric acid (4:1, 15 ml) at 45° C. for 3 h. This was followed by concentration to dryness. Purification by preparative HPLC (methanol:water (+1% trifluoroacetic acid) gradient) gave 31 mg of the title compound (42% of theory).

LC-MS (Method 2): $R_t$=0.95 min; MS (EIpos): m/z=428 $[M+H]^+$.

$^1$H NMR (400 MHz, DMSO-$d_6$): δ [ppm]=1.47 (s, 6H), 2.76-2.87 (m, 2H), 4.89 (t, 2H), 6.39-6.62 (m, 1H), 8.55 (dd, 1H), 8.78 (dd, 1H), 12.17 (s br, 1H).

Example 8

3-{1-[(3,3-Difluorocyclobutyl)methyl]-5-fluoro-1H-pyrazolo[3,4-b]pyridin-3-yl}-7,7-dimethyl-5,7-dihydro-6H-pyrrolo[2,3-e][1,2,4]triazin-6-one

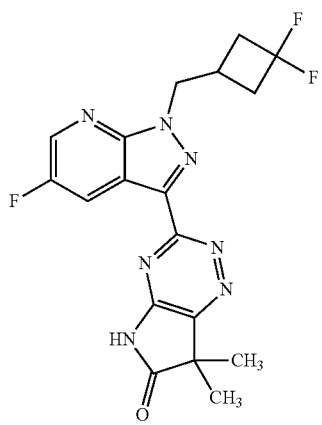 [SMILES: CC1(C)C(=O)Nc2nc(-c3nn(CC4CC(F)(F)C4)c4ncc(F)cc34)nnc21]

100 mg (0.189 mmol) of the compound from Example 38A were reacted analogously to the procedure of Example 7. Purification by preparative HPLC (acetonitrile:water (+1% trifluoroacetic acid) gradient) gave 15 mg of the title compound (19% of theory).

LC-MS (Method 1): $R_t$=1.00 min; MS (EIpos): m/z=404 $[M+H]^+$.

$^1$H NMR (400 MHz, DMSO-$d_6$): δ [ppm]=1.47 (s, 6H), 2.47-2.54 (m, 2H, obscured by solvent), 2.64-2.73 (m, 2H), 2.78-2.86 (m, 1H), 4.75 (d, 2H), 8.54 (dd, 1H), 8.76 (dd, 1H), 12.14 (s br, 1H).

Example 9

Ethyl 5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxylate

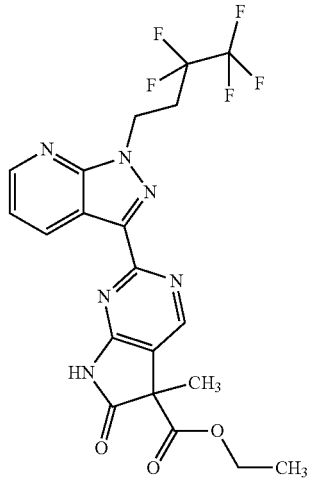 [SMILES: CCOC(=O)C1(C)C(=O)Nc2nc(-c3nn(CCC(F)(F)C(F)(F)F)c4ncccc34)ncc21]

190 mg (0.304 mmol, purity about 90%) of Example 41A were hydrogenated analogously to Example 3. This gave 36 mg (18% of theory) of the title compound in a purity of 77%.

LC-MS (Method 2): $R_t$=1.08 min; MS (ESIpos): m/z=485 $(M+H)^+$

Example 10

N-Cyclopropyl-5-methyl-6-oxo-2-[1-(3,3,4,4,4-pentafluorobutyl)-1H-pyrazolo[3,4-b]pyridin-3-yl]-6,7-dihydro-5H-pyrrolo[2,3-d]pyrimidine-5-carboxamide (racemate)

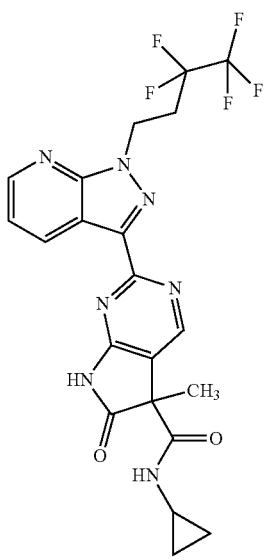 [SMILES: CC1(C(=O)NC2CC2)C(=O)Nc2nc(-c3nn(CCC(F)(F)C(F)(F)F)c4ncccc34)ncc21]

34 mg (0.054 mmol, purity 77%) of Example 9 were taken up in methanol (0.5 ml), and 30 mg (0.540 mmol) of cyclopropylamine were added. The mixture was then treated in a microwave at 80° C. for 1 day. Purification by preparative HPLC (acetonitrile:water (+0.1% formic acid) gradient) gave 13 mg of the title compound (50% of theory).

LC-MS (Method 2): $R_t$=0.99 min; MS (EIpos): m/z=496 $[M+H]^+$.

$^1$H NMR (400 MHz, DMSO-$d_6$): δ [ppm]=0.41-0.46 (m, 2H), 0.59-0.61 (m, 2H), 1.61 (s, 3H), 2.62-2.66 (m, 1H), 2.95-3.08 (m, 2H), 4.93 (t, 2H), 7.44 (dd, 1H), 7.75 (d, 1H), 8.58 (s, 1H), 8.68 (dd, 1H), 8.87 (dd, 1H), 11.79 (s, 1H).

B. Assessment of Pharmacological Efficacy

The pharmacological effect of the compounds according to the invention can be shown in the following assays:

B-1. Vasorelaxant Action In Vitro

Rabbits are stunned by a blow to the neck and exsanguinated. The aorta is removed, freed from adhering tissue and divided into rings of a width of 1.5 mm. The rings are placed individually under an initial tension in 5 ml organ baths with Krebs-Henseleit solution which is at 37° C., is gassed with carbogen and has the following composition (in each case mM): sodium chloride: 119; potassium chloride: 4.8; calcium chloride dihydrate: 1; magnesium sulfate heptahydrate: 1.4; potassium dihydrogenphosphate: 1.2; sodium bicarbonate: 25; glucose: 10. The contractile force is determined with Statham UC2 cells, amplified and digitalized using A/D transducers (DAS-1802 HC, Keithley Instruments Munich), and recorded in parallel on linear recorders. To obtain a contraction, phenylephrine is added to the bath cumulatively in increasing concentration. After several control cycles, the substance to be investigated is added in each further run in increasing dosage in each case, and the height of the contraction achieved is compared with the height of the contraction reached in the last preceding run. This is used to calculate the concentration needed to reduce the magnitude of the control value by 50% (1050 value). The standard administration volume is 5 μl; the DMSO content in the bath solution corresponds to 0.1%.

Representative $IC_{50}$ values for the compounds according to the invention are shown in the table below (Table 1):

TABLE 1

| Example No. | $IC_{50}$ [nM] |
|---|---|
| 1 | 263 |
| 2 | 129 |
| 3 | 46 |
| 4 | 101 |
| 5 | 23 |
| 6 | 102 |

B-2. Effect on a Recombinant Guanylate Cyclase Reporter Cell Line

The cellular activity of the compounds according to the invention is determined using a recombinant guanylate cyclase reporter cell line, as described in F. Wunder et al., Anal. Biochem. 339, 104-112 (2005).

Representative values (MEC=minimum effective concentration) for the compounds according to the invention are shown in the table below (Table 2):

TABLE 2

| Example No. | MEC [μM] |
|---|---|
| 1 | 0.3 |
| 2 | 0.1 |
| 3 | 0.03 |
| 4 | 0.03 |
| 5 | 0.1 |
| 6 | 0.1 |
| 7 | 0.3 |
| 8 | 3.0 |

B-3. Radiotelemetric Measurement of Blood Pressure on Conscious Spontaneously Hypertensive Rats A commercially available telemetry system from DATA SCIENCES INTERNATIONAL DSI, USA, is employed for the blood pressure measurement on conscious rats described below.

The system consists of 3 main components:
implantable transmitters (Physiotel® telemetry transmitter)
receivers (Physiotel® receiver) which are linked via a multiplexer (DSI Data Exchange Matrix) to a
data acquisition computer.

The telemetry system makes it possible to continuously record blood pressure, heart rate and body motion of conscious animals in their usual habitat.

Animal Material

The investigations are carried out on adult female spontaneously hypertensive rats (SHR Okamoto) with a body weight of >200 g. SHR/NCrI from the Okamoto Kyoto School of Medicine, 1963 were a cross of male Wistar Kyoto rats with highly elevated blood pressure and female rats having a slightly elevated blood pressure and at F13 handed over to the U.S. National Institutes of Health.

After transmitter implantation, the experimental animals are housed singly in type 3 Makrolon cages. They have free access to standard feed and water.

The day/night rhythm in the experimental laboratory is changed by the room lighting at 6.00 am and at 7.00 pm.

Transmitter Implantation

The telemetry transmitters TA11 PA-C40 used are surgically implanted under aseptic conditions in the experimental animals at least 14 days before the first experimental use. The animals instrumented in this way can be employed repeatedly after the wound has healed and the implant has settled.

For the implantation, the fasted animals are anesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and the wound is closed layer by layer.

An antibiotic (Tardomyocel COMP, Bayer, 1 ml/kg s.c.) is administered postoperatively for prophylaxis of infection.

Substances and Solutions

Unless indicated otherwise, the substances to be investigated are administered orally by gavage in each case to a group of animals (n=6). The test substances are dissolved in suitable solvent mixtures, or suspended in 0.5% strength Tylose, appropriate for an administration volume of 5 ml/kg of body weight.

A solvent-treated group of animals is employed as control.

Test Procedure

The telemetry measuring unit present is configured for 24 animals. Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch and are switched to transmission in the run-up to the experiment. The emitted signals can be detected online by a data acquisition system (Dataquest™ A.R.T. for Windows, DSI) and be appropriately processed. The data are stored in each case in a file created for this purpose and bearing the experiment number.

In the standard procedure, the following are measured for 10-second periods in each case:
systolic blood pressure (SBP)
diastolic blood pressure (DBP)
mean arterial pressure (MAP)
heart rate (HR)
activity (ACT).

The acquisition of measurements is repeated under computer control at 5-minute intervals. The source data obtained as absolute value are corrected in the diagram with the currently measured barometric pressure (Ambient Pressure Reference Monitor; APR-1) and stored as individual data. Further technical details are given in the extensive documentation from the manufacturing company (DSI).

Unless indicated otherwise, the test substances are administered at 9.00 am on the day of the experiment. Following the administration, the parameters described above are measured over 24 hours.

Evaluation

After the end of the experiment, the acquired individual data are sorted using the analysis software (Dataquest™ A.R.T.™ Analysis). The blank value is assumed to be the time 2 hours before administration, and so the selected data set encompasses the period from 7.00 am on the day of the experiment to 9.00 am the following day.

The data are smoothed over a presettable time by determination of the average (15-minute average) and transferred as a text file to a storage medium. The measured values presorted and compressed in this way are transferred into Excel templates and tabulated. For each day of the experiment, the data obtained are stored in a dedicated file bearing the number of the experiment. Results and test protocols are filed in paper form sorted by numbers.

Literature

Klaus Witte, Kai Hu, Johanna Swiatek, Claudia Mussig, Georg Ertl and Björn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994

B-4. Determination of Pharmacokinetic Parameters Following Intravenous and Oral Administration The pharmacokinetic parameters of the compounds of the formula (I) according to the invention are determined in male CD-1 mice, male Wistar rats and female beagles. Intravenous administration in the case of mice and rats is effected by means of a species-specific plasma/DMSO formulation, and in the case of dogs by means of a water/PEG400/ethanol formulation. In all species, oral administration of the dissolved substance is performed via gavage, based on a water/PEG400/ethanol formulation. The taking of blood from rats is simplified by inserting a silicone catheter into the right Vena jugularis externa prior to substance administration. The operation is effected at least one day prior to the experiment with isofluran anesthesia and administration of an analgesic (atropine/rimadyl (3/1) 0.1 ml s.c.). The blood is taken (generally more than 10 time points) within a time window including terminal time points of at least 24 to a maximum of 72 hours after substance administration. The blood is removed into heparinized tubes. The blood plasma is then obtained by centrifugation; if required, it can be stored at −20° C. until further processing.

An internal standard (which may also be a chemically unrelated substance) is added to the samples of the compounds of the formula (I) according to the invention, calibration samples and qualifiers, and this is followed by protein precipitation using excess acetonitrile. Addition of a buffer solution matched to the LC conditions, and subsequent vortexing, is followed by centrifugation at 1000 g. The supernatant is analyzed by means of LC-MS/MS using C18 reversed-phase columns and variable mobile phase mixtures. The substances are quantified via the peak heights or areas from extracted ion chromatograms of specific selected ion monitoring experiments.

The plasma concentration/time plots determined are used to calculate the pharmacokinetic parameters such as AUC, $C_{max}$, $t_{1/2}$ (terminal half life), MRT (mean residence time) and CL (clearance), using a validated pharmacokinetic calculation program.

Since the substance quantification is performed in plasma, it is necessary to determine the blood/plasma distribution of the substance in order to be able to adjust the pharmacokinetic parameters correspondingly. For this purpose, a defined amount of substance is incubated in heparinized whole blood of the species in question in a rocking roller mixer for 20 min. After centrifugation at 1000 g, the plasma concentration is measured (by means of LC-MS/MS; see above) and determined by calculating the ratio of the $C_{blood}/C_{plasma}$ value.

B-5. Metabolic Study

To determine the metabolic profile of the compounds according to the invention, they are incubated with recombinant human cytochrome P450 (CYP) enzymes, liver microsomes or primary fresh hepatocytes from various animal species (e.g. rats, dogs), and also of human origin, in order to obtain and to compare information about a very substantially complete hepatic phase I and phase II metabolism, and about the enzymes involved in the metabolism.

The compounds according to the invention were incubated with a concentration of about 0.1-10 μM. To this end, stock solutions of the compounds according to the invention having a concentration of 0.01-1 mM in acetonitrile were prepared, and then pipetted with 1:100 dilution into the incubation mixture. Liver microsomes and recombinant enzymes were incubated at 37° C. in 50 mM potassium phosphate buffer pH 7.4 with and without NADPH-generating system consisting of 1 mM NADP+, 10 mM glucose-6-phosphate and 1 unit glucose-6-phosphate dehydrogenase. Primary hepatocytes were incubated in suspension in Williams E medium, likewise at 37° C. After an incubation time of 0-4 h, the incubation reactions were stopped with acetonitrile (final concentration about 30%) and the protein was centrifuged off at about 15000×g. The samples thus stopped were either analyzed directly or stored at −20° C. until analysis.

The analysis is effected by means of high-performance liquid chromatography with ultraviolet and mass spectrometry detection (HPLC-UV-MS/MS). To this end, the supernatants of the incubation samples are chromatographed with suitable C18-reversed-phase columns and variable mobile phase mixtures of acetonitrile and 10 mM aqueous ammonium formate solution or 0.05% formic acid. The UV chromatograms in conjunction with mass spectrometry data serve for identification, structural elucidation and quantitative estimation of the metabolites, and for quantitative metabolic assessment of the compound according to the invention in the incubation mixtures.

C. Working Examples for Pharmaceutical Compositions

The compounds according to the invention can be converted to pharmaceutical formulations as follows:

Tablet:
Composition:
100 mg of the compound according to the invention, 50 mg of lactose (monohydrate), 50 mg of maize starch (native), 10 mg of polyvinylpyrrolidone
(PVP 25) (BASF, Ludwigshafen, Germany) and 2 mg of magnesium stearate. Tablet weight 212 mg, diameter 8 mm, radius of curvature 12 mm.
Production:
The mixture of the compound according to the invention, lactose and starch is granulated with a 5% solution (w/w) of the PVP in water. The granules are dried and mixed with the magnesium stearate for 5 minutes. This mixture is pressed with a conventional tableting press (for tablet dimensions see above). The guide value used for the pressing is a pressing force of 15 kN.

Suspension which can be Administered Orally:
Composition:
1000 mg of the compound according to the invention, 1000 mg of ethanol (96%), 400 mg of Rhodigel® (xanthan gum from FMC, Pennsylvania, USA) and 99 g of water.

A single dose of 100 mg of the compound according to the invention corresponds to 10 ml of oral suspension.
Production:
The Rhodigel is suspended in ethanol and the compound according to the invention is added to the suspension. The water is added while stirring. The mixture is stirred for about 6 h until swelling of the Rhodigel is complete.

Solution which can be Administered Orally:
Composition:
500 mg of the compound according to the invention, 2.5 g of polysorbate and 97 g of polyethylene glycol 400. A single dose of 100 mg of the compound according to the invention corresponds to 20 g of oral solution.
Production:
The compound according to the invention is suspended in the mixture of polyethylene glycol and polysorbate while stirring. The stirring operation is continued until dissolution of the compound according to the invention is complete.

i.v. Solution:
The compound according to the invention is dissolved in a concentration below the saturation solubility in a physiologically acceptable solvent (e.g. isotonic saline, glucose solution 5% and/or PEG 400 solution 30%). The solution is subjected to sterile filtration and dispensed into sterile and pyrogen-free injection vessels.

The invention claimed is:
1. A compound of the formula (I)

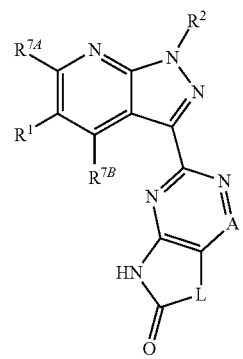

in which
A is nitrogen or $CR^3$,
where
$R^3$ represents hydrogen,
L is a #-$CR^{4A}R^{4B}$—$(CR^{5A}R^{5B})_p$-## group
where
# is the point of attachment to the carbonyl group,
## is the point of attachment to the pyrimidine ring or triazine ring,
p is a number 0,
$R^{4A}$ is hydrogen, fluorine, methyl or hydroxy,
$R^{4B}$ is hydrogen, fluorine, trifluoromethyl, 2,2,2-trifluoroethyl, methyl or a group of the formula -M-$R^8$,
in which
M is a bond,
$R^8$ is —(C=O)$_r$-$NR^9R^{10}$,
in which
r is the number 1,
$R^9$ and $R^{10}$ independently of one another are each hydrogen or cyclopropyl,
$R^{5A}$ is hydrogen, fluorine, ($C_1$-$C_4$)-alkyl or hydroxyl,
$R^{5B}$ is hydrogen, fluorine, ($C_1$-$C_4$)-alkyl or trifluoromethyl,
$R^1$ is hydrogen or fluorine,
$R^2$ is 4,4,4-trifluorobut-1-yl, 3,3,4,4-tetrafluorobut-1-yl, 3,3,4,4,4-pentafluorobut-1-yl, cyclobutylmethyl or cyclopentylmethyl, where cyclobutylmethyl and cyclopentylmethyl may be substituted by 1 or 2 fluorine substituents,
$R^{7A}$ is hydrogen is hydrogen or methyl, and
$R^{7B}$ is hydrogen,
or the salts, solvates or solvates of the salts thereof.

2. Process for preparing compounds of the formula (I) as defined in claim 1, characterized in that the compound of the formula (II)

(II)

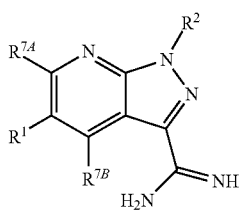

in which $R^1$, $R^2$, $R^{7A}$ and $R^{7B}$ each have the meanings given above,

[A] is reacted in an inert solvent in the presence of a suitable base with a compound of the formula (III)

(III)

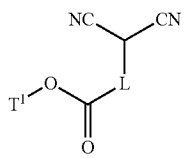

in which L has the meaning given in claim 1 and
$T^1$ is $(C_1\text{-}C_4)$-alkyl,
to give a compound of the formula (IV)

(IV)

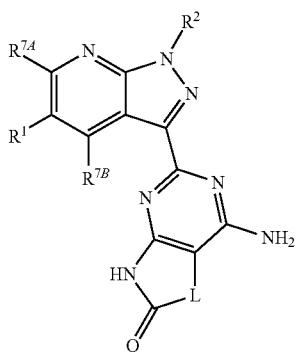

in which L, $R^1$, $R^2$, $R^{7A}$ and $R^{7B}$ each have the meanings given in claim 1, this is then converted with isopentyl nitrite and a halogen equivalent into a compound of the formula (V)

(V)

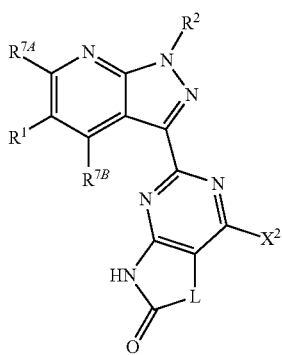

in which L, $R^1$, $R^2$, $R^{7A}$ and $R^{7B}$ each have the meanings given in claim 1 and $X^2$ is bromine or iodine, and this is then reacted in an inert solvent, in the presence of a suitable transition metal catalyst, to give a compound of the formula (I-A)

(I-A)

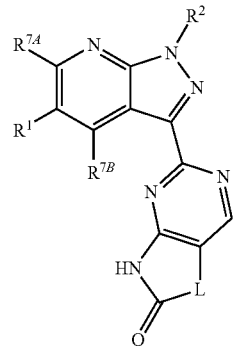

in which L, $R^1$, $R^2$, $R^{7A}$ and $R^{7B}$ each have the meanings given in claim 1, or

[B] is reacted in an inert solvent in the presence of a suitable base with hydrazine hydrate to give a compound of the foimula (VI)

(VI)

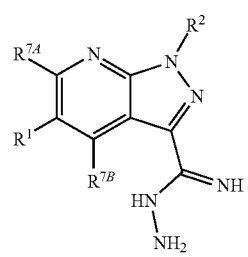

in which $R^1$, $R^2$, $R^{7A}$ and $R^{7B}$ each have the meanings given in claim 1, this is then reacted in an inert solvent with a compound of the formula (VII)

(VII)

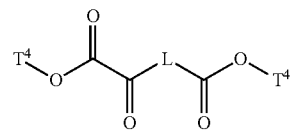

in which L has the meaning given in claim 1 and
$T^4$ is $(C_1\text{-}C_4)$-alkyl
to give a compound of the formula (VIII)

(VIII)

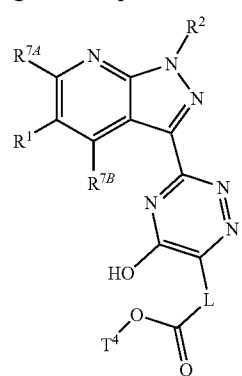

in which L, $R^1$, $R^2$, $R^{7A}$, and $R^{7B}$ each have the meanings given in claim 1, this is then converted with phosphoryl chloride into a compound of the formula (IX)

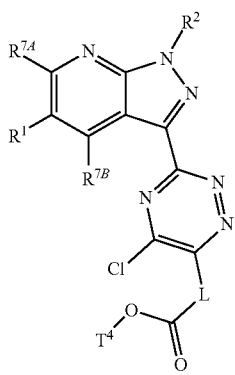

(IX)

in which L, R¹, R², R$^{7A}$, and R$^{7B}$ each have the meanings given in claim 1, and this is reacted directly with ammonia to give a compound of the formula (X)

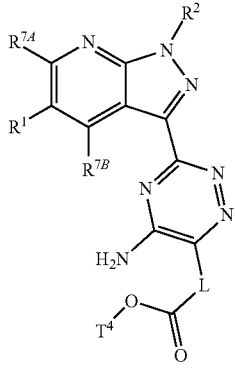

(X)

in which L, R¹, R², R$^{7A}$, and R$^{7B}$ each have the meanings given in claim 1, and finally cyclized in an inert solvent, optionally in the presence of a suitable base, to give a compound of the formula (I-B)

(I-B)

in which L, R¹, R², R$^{7A}$, and R$^{7B}$ each have the meanings given in claim 1, and the resulting compounds of the formulae (I-A) and (I-B) are, where appropriate, converted with the appropriate (i) solvents and/or (ii) acids or bases into their solvates, salts and/or solvates of the salts.

3. A medicament comprising a compound of the formula (I) as defined in claim 1 in combination with an inert, non-toxic, pharmaceutically suitable excipient.

4. A medicament comprising a compound of the formula (I) as defined in claim 1 in combination with a further active compound selected from the group consisting of organic nitrates, NO donors, cGMP-PDE inhibitors, antithrombotic agents, hypotensive agents and lipid metabolism modifiers.

5. A Method for treatment of heart failure, angina pectoris, hypertension, pulmonary hypertension, ischemias, or arteriosclerosis in humans comprising administering an effective amount of at least one compound of the formula (I) as defined in claim 1

.

\* \* \* \* \*